United States Patent [19]
Kaleko

[11] Patent Number: 6,156,497
[45] Date of Patent: Dec. 5, 2000

[54] RECOMBINASE-MEDIATED GENERATION OF ADENOVIRAL VECTORS

[75] Inventor: Michael Kaleko, Rockville, Md.

[73] Assignee: Genetic Therapy, Inc., Gaithersburg, Md.

[21] Appl. No.: 09/051,579

[22] PCT Filed: Jan. 3, 1997

[86] PCT No.: PCT/US97/00370

§ 371 Date: Apr. 13, 1998

§ 102(e) Date: Apr. 13, 1998

[87] PCT Pub. No.: WO97/25446

PCT Pub. Date: Jul. 17, 1997

Related U.S. Application Data

[63] Continuation-in-part of application No. 08/583,703, Jan. 5, 1996, abandoned.

[51] Int. Cl.[7] .............. C12Q 1/70; C12P 19/34; C12N 15/87; C12N 15/63; C07H 21/04
[52] U.S. Cl. ................ 435/5; 435/91.4; 435/320.1; 435/462; 536/23.1
[58] Field of Search .............. 435/5, 91.4, 235.1, 435/320.1; 536/23.1

[56] References Cited

U.S. PATENT DOCUMENTS

| | | | |
|---|---|---|---|
| 4,959,317 | 9/1990 | Sauer | 435/462 |
| 5,650,309 | 7/1997 | Wong-Staal et al. | 435/456 |
| 5,919,676 | 7/1999 | Graham et al. | 435/91.4 |

FOREIGN PATENT DOCUMENTS

| | | |
|---|---|---|
| WO94/23582 | 10/1994 | WIPO. |
| WO95/06743 | 3/1995 | WIPO. |
| WO96/40955 | 12/1996 | WIPO. |

OTHER PUBLICATIONS

Wang et al. A packaging cell line for propagation of recombinant adenovirus vectors containing two lethal gene–region deletions. Gene Therapy vol. 2:775–783, Jun. 1996.
Amalfitano et al. Improved adenovirus packaging cel lines to support the growth of replication–defective gene–delivery vectors. PNAS (USA) vol. 93:3352–3356, Apr. 1996.
Sharp, et al., *Virology,* vol. 75, pp. 442–456 (1976).
Saito, et al.,*J. Virol,* vol. 54, No. 3, pp. 711–719 (Jun. 1985).
Sternberg, et al.,*J. Mol. Biol.,* vol. 187, pp. 197–212 (1986).
Gilardi, et al., *Nucleic Acids Research,* pp. 9035–9049 (1986).
Sauer, *Mol. Cell. Biol.,* vol. 7, No. 6, pp. 2087–2096 (Jun. 1987).
Hanaka, et al., *Mol. Cell. Biol.,* vol. 7, No. 7, pp. 2578–2587 (Jul. 1987).
Watanabe, et al., *Mol. Cell. Biol.,* vol. 8, No. 3, pp. 1290–1300 (Mar. 1988).
Sauer, et al., *Proc. Nat. Acad. Sci.,* vol. 85, pp. 5166–5170 (Jul. 1988).
Sauer, et al., *Nucleic Acids Research,* vol. 17, No. 1, pp. 147–161 (1989).
Golic, et al., *Cell,* vol. 59, pp. 499–509 (Nov. 3, 1989).
O'Gorman, et al., *Science,* vol. 251, pp. 1351–1355 (Mar. 15, 1991).
Dale, et al., *Proc. Nat. Acad. Sci.,* vol. 88, pp. 10558–10562 (Dec. 1991).
Peakman, et al., *Nucleic Acids Research,* vol. 20, No. 3, pp. 495–500 (1992).
Orban, et al., *Proc. Nat. Acad. Sci.,* vol. 89, pp. 6861–6865 (Aug. 1992).
Gage, et al., *J. Virol.,* vol. 66, No. , pp. 5509–5515 (Sep. 1992).
Sauer, *Methods in Enzymology,* vol. 225, pp. 890–900 (1993).
Landy, *Curr. Opin. Genetics Devel.,* vol. 3, pp. 699–707 (1993).
Pronk, et al., *Nucleic Acids Research,* vol. 21, No. 10, pp. 2293–2300 (1993).
Gu, et al., *Cell,* vol. 73, pp. 1155–1164 (Jun. 18, 1993).
Gu, et al., *Science,* vol. 265, pp. 103–106 (Jul. 1, 1994).
Mitani, et al., *Proc. Nat. Acad. Sci.,* vol. 92, pp. 3854–3858 (Apr. 1995).
Metzger, et al., *Proc. Nat. Acad. Sci.,* vol. 92, pp. 6991–6995 (Jul. 1995).
Anton, et al., *J. Virol.,* vol. 69, No. 8, pp. 4600–4606 (Aug. 1995).
Kochanek, et al., *A New Large Capacity Adenoviral Vector Devoid of Viral Coding Sequences* (1995).

*Primary Examiner*—Robert A. Schwartzman
*Assistant Examiner*—William Sandals
*Attorney, Agent, or Firm*—Elliot M. Olstein; Raymond J. Lillie

[57] ABSTRACT

A method for generating adenoviral vectors from polynucleotides such as plasmids wherein there occurs recombinase-mediated transfer of an adenoviral ITR and terminal proteins bound to the ITR to a plasmid, thus enabling the plasmid to replicate as an adenoviral vector. Such method enables the rapid generation of adenoviral vectors at high titers from plasmids without the use of selectable markers and screening procedures. Such method enables the rapid generation of adenoviral vectors devoid of adenovirus backbone genes. The method also may be employed to generate hybrid adenoviral-retroviral vectors that convert transduced cells into producer cells that produce retroviral vectors to effect high level, permanent genetic modification of cells in vivo.

14 Claims, 26 Drawing Sheets

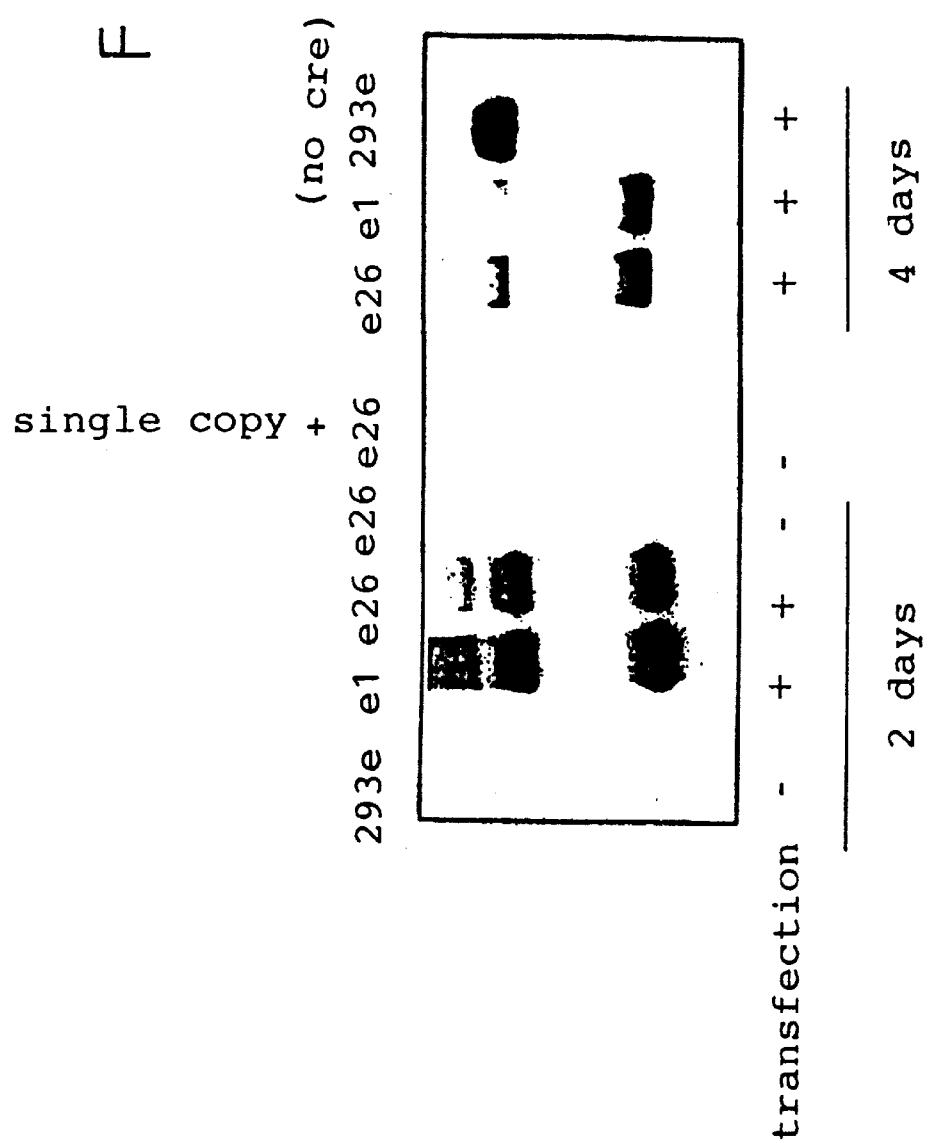

MATCH WITH FIG. 2B

FIG. 2A

```
       -300
5'- CATCATCAATAATATACCTTATTTTGGATTGAAGCCAATATGATAATGAG
    | | | | |
3'- GTAGTAGTTATTATATGGAATAAAACCTAACTTCGGTTATACTATTACTC

-200
5'- TAGGTTTTAGGGGCGGAGTAACTTGTATGTGTTGGGAATTGTAGTTTTCTT
    | | | | |
3'- ATCCAAAATCCCCGCCTCATTGAACATACACAACCCTTAACATCAAAAGAA
    ↑End ITR

-100
5'- GTTGTGGGTTTTTTTGGCTTTCGTTTCTGGGCGTAGGTTCGCCGTGCGGTTT
    | | | | |
3'- CAACACCCAAAAAAACCGAAAGCAAAGACCCGCATCCAAGCGGCACGCCAAA wild type Ad 5
```

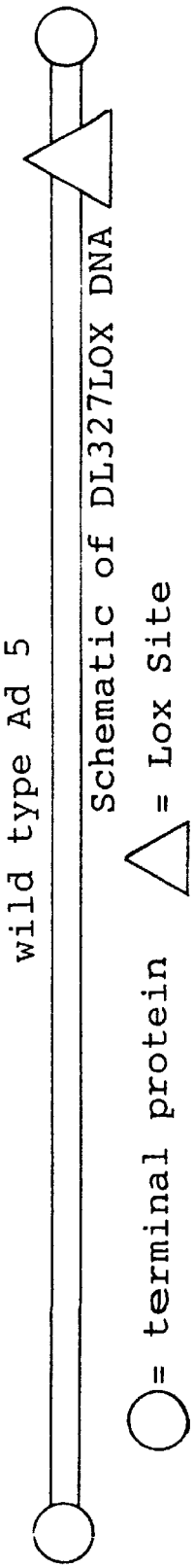

Schematic of DL327LOX DNA

△ = Lox Site

○ = terminal protein

MATCH WITH FIG. 2A

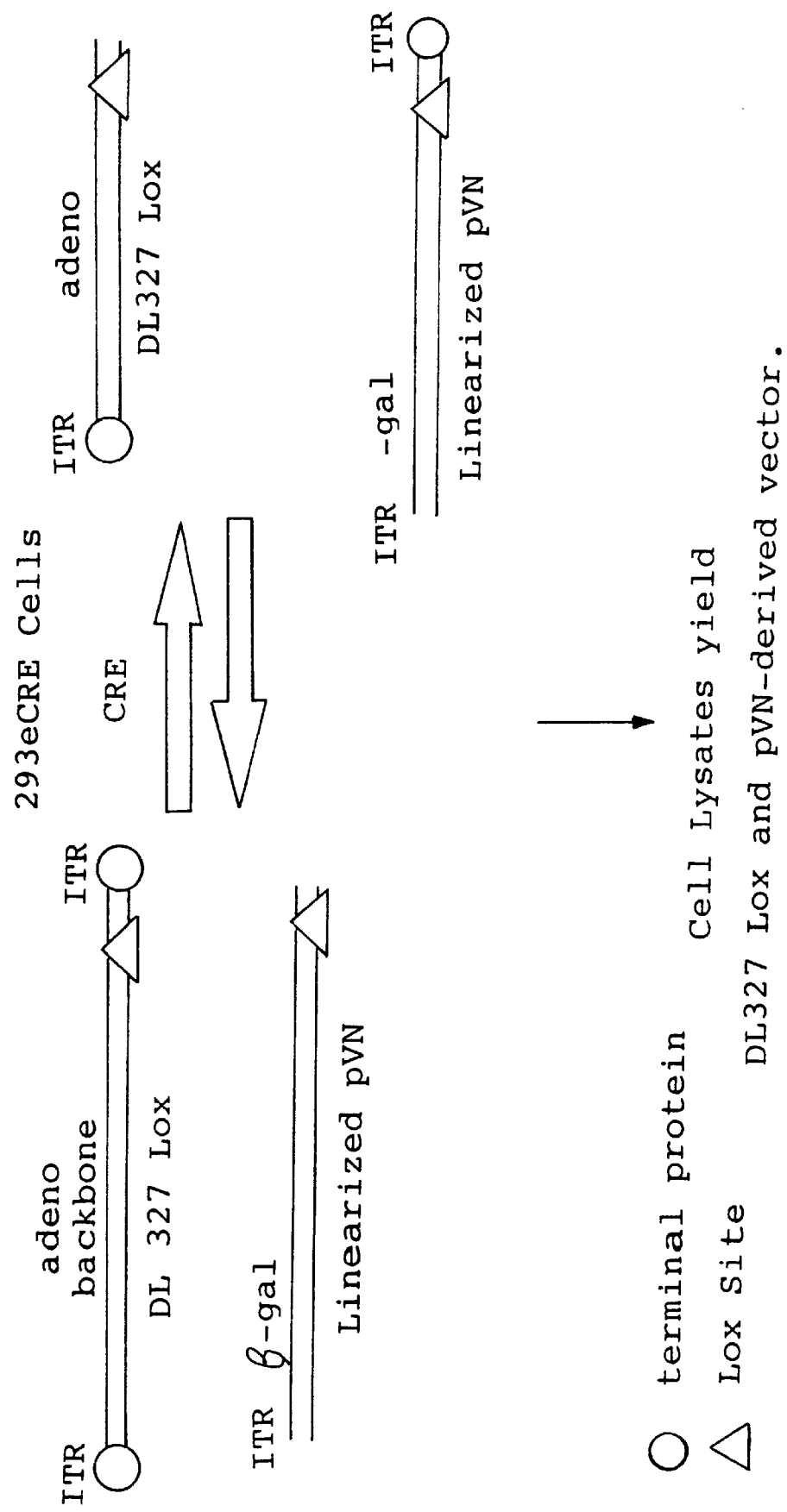

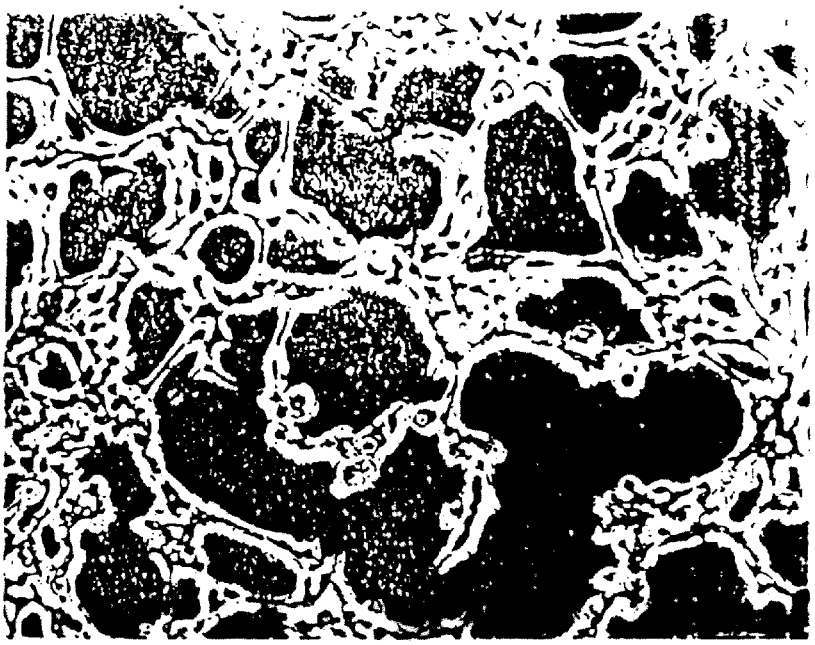
FIG. 8B — Control / DL 327 Lox lysate
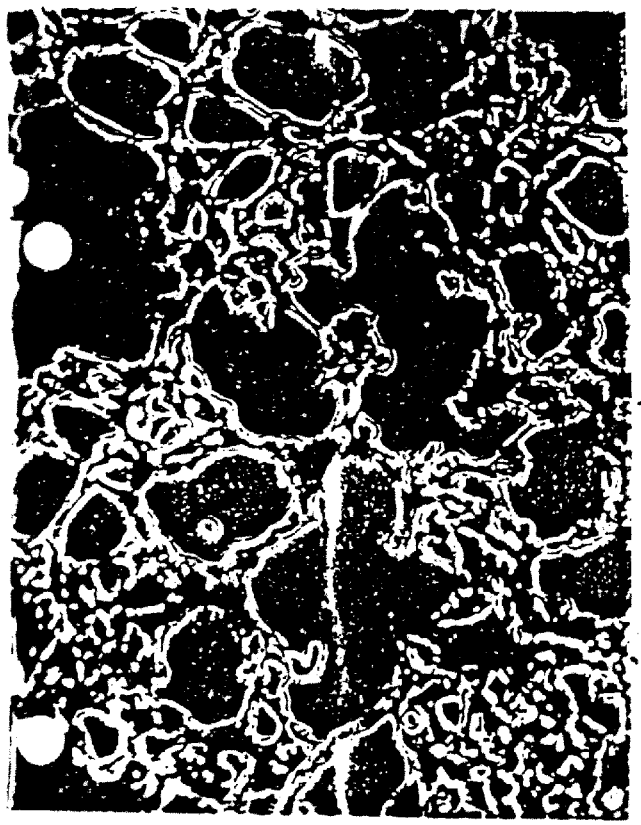
FIG. 8A — pVN/DL327 Lox lysate Control 2 pVN lysate

β-gal staning of S8 cells transduced with a CVL generated from transfection of a cell-free Cre/lox recombination of PVNL5+DL327 lox with terminal protein.

FIG. 18
Schematic of Packaging Signal Regions
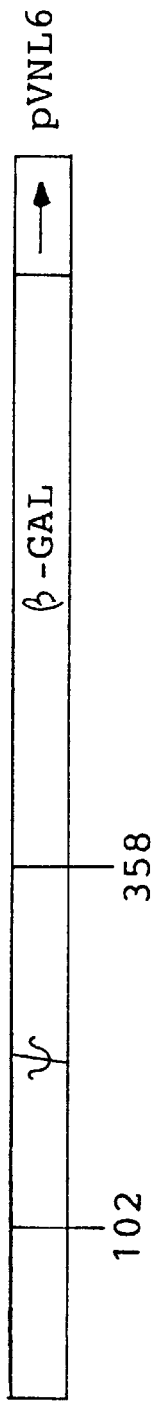
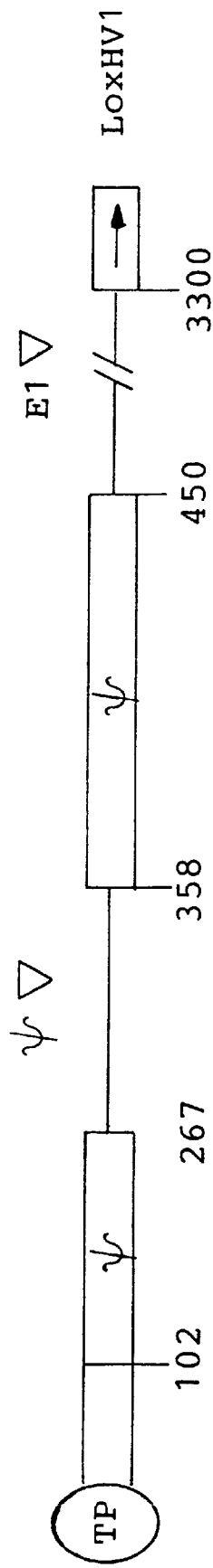

RECOMBINASE-MEDIATED GENERATION OF ADENOVIRAL VECTORS

This application is a continuation-in-part of application Ser. No. 08/583,703, filed Jan. 5, 1996 now abandoned, the contents of which are hereby incorporated by reference.

This invention relates to the generation of adenoviral vectors. More particularly, this invention relates to the generation of adenoviral vectors directly from polynucleotide constructs such as plasmids, whereby a site-specific recombinase mediates transfer of an adenoviral ITR with a terminal protein bound thereto to the plasmid, thereby enabling the plasmid to replicate efficiently as if it were an adenovirus. This invention also relates to adenoviral vectors that are devoid completely of adenoviral backbone genes and to adenoviral vectors that transfer retroviral vector sequences, as well as the genes for retroviral structural proteins, including gag, pol, and env.

The term "adenoviral vector," as used herein, means a gene transfer vehicle which is an adenoviral particle containing recombinant adenoviral DNA that incorporates a desired DNA sequence to be transferred into an appropriate cell.

BACKGROUND OF THE INVENTION

Adenovirus genomes are linear, double-stranded DNA molecules about 36 kilobase pairs long. Each extremity of the viral genome has a short sequence known as the inverted terminal repeat (or ITR), which is necessary for viral replication. The well-characterized molecular genetics of adenovirus render it an advantageous vector for gene transfer. The knowledge of the genetic organization of adenoviruses allows substitution of large fragments of viral DNA with foreign sequences. In addition, recombinant adenoviruses are structurally stable and no rearranged viruses are observed after extensive amplification.

Adenoviruses thus may be employed as delivery vehicles for introducing desired genes into eukaryotic cells, whereby the adenovirus delivers such genes to eukaryotic cells by binding cellular receptors, internalizing via coated pits, disrupting endosomes, and releasing particles to the cytoplasm followed by nuclear translocation and molecular expression of the adenovirus genetic program.

In general, in order to construct an adenoviral vector including a heterologous gene, or transgene, a plasmid is prepared which contains the transgene expression cassette and some adenoviral sequences, usually from the left end, or 5' end, of the virus. The plasmid then is co-transfected with DNA containing most of the adenoviral sequence, and homologous recombination occurs, yielding plaques on the adenoviral producer cells, such as, for example, 293 cells. The plaques are picked, amplified, screened, and scaled up further. Such process may take several months or more. If one desires to change the vector backbone, the process then involves further manipulation. If a single adenoviral gene is to be deleted from the adenoviral backbone, the first step is to generate a packaging cell that expresses the gene in trans. Next, a new plasmid is generated which encodes a portion of the adenoviral backbone with the adenoviral gene deleted. This plasmid is co-transfected with DNA encoding the remainder of the adenovirus. Homologous recombination then occurs, and adenoviral plaques are generated, screened, and scaled up, thus yielding a virus with an altered backbone. This virus then is used to generate a vector with a transgene by homologous recombination with the transgene-encoding plasmid as hereinabove described. The generation of such an adenoviral vector may take one year or more.

SUMMARY OF THE INVENTION

The present invention provides a cell and a method for generating adenoviral vectors directly from polynucleotides, such as plasmids, without the need to obtain, screen, or cycle up plaques. The present invention saves a substantial amount of time and enables vectors with transgene and/or backbone gene changes to be made and tested very rapidly. In particular, the present invention provides for the generation of an adenoviral vector from a polynucleotide, such as a plasmid, through the recombinase-mediated transfer of an adenoviral ITR with a covalently attached adenoviral terminal protein to the plasmid. According to the present invention, a high concentration of adenoviral vector can be obtained directly from transfected cells.

The present invention also is directed to the rapid generation of adenoviral vectors from which all adenovirus backbone genes have been deleted. Such "gutless" vectors provide a significant advance over presently available vectors because the toxicity and immunogenicity of adenoviral backbone gene products is avoided. Furthermore, such a vector could incorporate up to 37,200 base pairs of heterologous sequence, as opposed to the 7,000 base pair limit incurred by standard vectors.

Another aspect of the invention relates to the rapid generation of an adenoviral vector capable of transferring retroviral vector sequences, as well as the genes for retroviral structural proteins, including gag, pol, and env. Such a hybrid adenoviral-retroviral vector, also known as a HARV, transforms transduced cells into producers of retroviral vectors. Thus, a single injection of HARV vectors can effect spread of a retroviral vector containing a heterologous gene throughout a tissue. Because retroviral vector transduction involves integration of the vector sequences into the host cell genomic DNA, a single administration of the HARV vector would result in widespread and permanent genetic modification of the target tissue.

BRIEF DESCRIPTION OF THE DRAWINGS

The invention now will be described with respect to the drawings, wherein:

FIG. 1 is a Southern Blot analysis for recombination of a plasmid containing two Lox sites which was transfected into 293e Cre cells;

FIG. 7 is a schematic for generating an adenoviral vector from pVN;

FIG. 18 is a schematic of packaging signal regions of pVNL6 and LoxHV1, and a schematic of the adenoviral E1 expression construct in AE1-2A.S8 cells;

DETAILED DESCRIPTION OF THE INVENTION

Figure 2B:
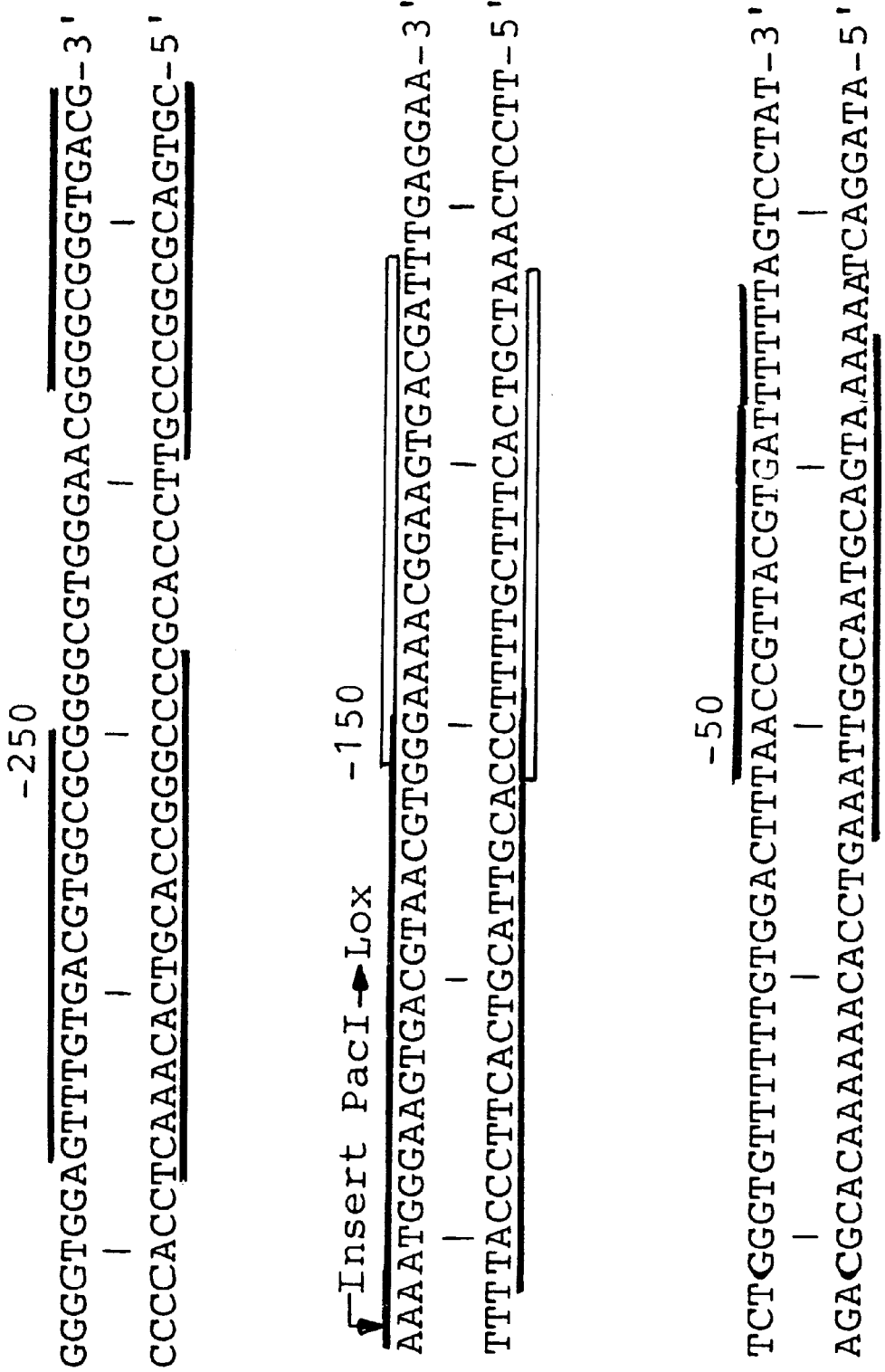
FIG. 2 is a diagram of the adenovirus 5 E4 promoter sequence SEQ ID NO:7 and a schematic of the helper virus DL327 Lox.

In accordance with an aspect of the present invention, there is provided a cell for producing an adenoviral vector for expressing heterologous DNA. The cell includes a first polynucleotide, a second polynucleotide, and a third polynucleotide. The first polynucleotide, from which the adenoviral vector will be derived, includes the heterologous DNA to be expressed, and one adenoviral ITR. The first polynucleotide further includes an adenoviral packaging signal, and a recombinase target site. In general, the ITR and recombinase target site are positioned such that they flank the DNA sequences which are to be incorporated in the adenoviral vector.

The second polynucleotide includes at least one adenoviral ITR which includes a terminal protein bound to the ITR, and a recombinase target site. The ITR in the second polynucleotide is a 5' ITR, when the first polynucleotide includes an adenoviral 3' ITR. The ITR in the second polynucleotide is an adenoviral 3' ITR when the first polynucleotide includes an adenoviral 5' ITR. The third polynucleotide includes DNA encoding a site-specific recombinase. The cell further contains DNA encoding adenoviral proteins for replication and packaging of the first polynucleotide as an adenoviral vector to the extent such DNA is not present in the first, second and third polynucleotides.

In one embodiment, the DNA encoding adenoviral proteins for replication and packaging of the first polynucleotide as an adenoviral vector particle is included in the second polynucleotide. In another embodiment, the DNA encoding adenoviral proteins for replication and packaging of the first polynucleotide as an adenoviral vector is included in the first polynucleotide.

In yet another embodiment, a portion of the DNA encoding adenoviral proteins for replication and packaging of the first polynucleotide as an adenoviral vector is included in the first polynucleotide, and a portion of the DNA encoding adenoviral proteins for replication and packaging of said first polynucleotide as an adenoviral vector is included in said second polynucleotide.

In a further embodiment, a portion of the DNA encoding adenoviral proteins for replication and packaging of the first polynucleotide as an adenoviral vector is independent of the first polynucleotide and the second polynucleotide, i.e., such portion of the DNA encoding adenoviral proteins for replication and packaging of the first polynucleotide as an adenoviral vector is provided by and contained in the cell prior to transfection of the cell with the first, second, and third polynucleotides.

In one embodiment, the first polynucleotide includes an adenoviral 5' ITR and an adenoviral packaging signal, and the second polynucleotide includes an adenoviral 3' ITR having a terminal protein bound to the adenoviral 3' ITR. In another embodiment, the first polynucleotide includes an adenoviral 3' ITR and an adenoviral packaging signal, and the second polynucleotide includes an adenoviral 5' ITR having a terminal protein bound to the adenoviral 5' ITR.

The generation of the adenoviral vector is accomplished by transfecting the cell with the first, second, and third polynucleotides. Alternatively, the DNA encoding the site-specific recombinase may be contained in the cell within an appropriate expression vehicle, such as a plasmid, or is integrated into a chromosome of the cell, prior to transfection of the cell with the first and second polynucleotides. Upon transfection of the cell with the polynucleotides, the recombinase expressed by the cell interacts with the recombinase target sites in the first and second polynucleotides. Such recombinase target sites are in the same orientation. The interaction of the recombinase with the recombinase target sites enables the transfer of an ITR with an adenoviral terminal protein bound thereto from the second polynucleotide to the first polynucleotide, which generates an adenoviral vector from the first polynucleotide. When the first polynucleotide includes an adenoviral 5' ITR, an adenoviral 3' ITR and the terminal protein bound thereto, are transferred from the second polynucleotide to the first polynucleotide. When the first polynucleotide includes an adenoviral 3' ITR, an adenoviral 5' ITR and the terminal protein bound thereto are transferred from the second polynucleotide to the first polynucleotide.

When the first polynucleotide is a plasmid, prior to transfection, preferably the plasmid is linearized. Thus, in one embodiment, the plasmid, prior to linearization, further includes a unique restriction site 5' to the 5' ITR and 3' to the recombinase target site, when the plasmid includes a 5' ITR. When the plasmid includes a 3' ITR, the plasmid further includes, in one embodiment, a unique restriction site which is 3' to the 3' ITR and 5' to the recombinase target site. The term "unique restriction site" as used herein, means that such restriction site appears only once in the first polynucleotide. The unique restriction site also may be a rare restriction enzyme site. The term "rare restriction enzyme site" as used herein, means a restriction site which occurs in eukaryotic genes at a frequency no greater than once in every 10,000 base pairs.

In one embodiment, the first polynucleotide is a plasmid which includes, in a 5' to 3' direction, a unique restriction site, an adenoviral 5' ITR, an adenoviral packaging signal, the heterologous DNA, and a recombinase target site. The at least one ITR in the second polynucleotide is an adenoviral 3' ITR. In another embodiment, the first polynucleotide is linearized prior to transfection into the cell and includes, in a 5' to 3' direction, the components mentioned hereinabove, with the exception of the unique restriction site, and the at least one ITR in the second polynucleotide is an adenoviral 3' ITR.

In a further embodiment, the first polynucleotide further includes an adenoviral 3' ITR.

In yet another embodiment, the first polynucleotide is a plasmid including, in a 5' to 3' direction, a recombinase target site, an adenoviral packaging signal, the heterologous DNA, an adenoviral 3' ITR, and a unique restriction site. The at least one ITR in the second polynucleotide is an adenoviral 5' ITR. In one embodiment, the first polynucleotide is linearized prior to transfection into the cell, and the first polynucleotide includes, in a 5' to 3' direction, the components mentioned hereinabove, with the exception of the unique restriction site, and the at least one ITR in the second polynucleotide is an adenoviral 5' ITR.

In a further embodiment, the first polynucleotide further includes an adenoviral 5' ITR.

Although the scope of the present invention is not intended to be limited to any theoretical reasoning, upon transfection of the cell with the polynucleotides as hereinabove described, the interaction of the site-specific recombinase expressed by the cell with the recombinase target sites in the first polynucleotide and the second polynucleotide mediates sufficient site-specific intermolecular recombination to effect the transfer of an adenoviral ITR with a terminal protein bound to the ITR from the second polynucleotide to the first polynucleotide, which in one embodiment may be in the form of a plasmid. The ITR, with the terminal protein bound thereto, serves as a template for replication of the first polynucleotide as an adenovirus. Applicant has found that such transfer of the ITR and terminal protein from the second polynucleotide to the first polynucleotide improves dramatically the replication of the first polynucleotide, which now replicates as an adenovirus. Due to such improved replication, the first polynucleotide, if desired, need not contain a selectable marker. When the first polynucleotide is a plasmid after one round of replication, terminal proteins become attached covalently to both ITR's, and the ITR's and sequence between the ITR's are lifted from the plasmid and continue to replicate efficiently as an adenoviral vector. The derivation of adenoviral vector from a polynucleotide as hereinabove described, such as a plasmid, is efficient enough to enable the production of a high level of vector directly from the transfected cells, thus eliminating the need to obtain and screen plaques to generate new vectors.

The recombinase may be expressed by the cell by a variety of methods. In one embodiment, the third polynucleotide is a plasmid including a DNA sequence encoding a recombinase. Such plasmid may replicate episomally, or may be integrated into the cellular chromosomal DNA. The DNA encoding the recombinase is under the control of a suitable promoter, such as a strong constitutive promoter, such as the CMV promoter, or an inducible promoter, such as, for example, a glucocorticoid response element (GREW) promoter which is induced by dexamethasone.

In another embodiment, a DNA sequence encoding a site-specific recombinase is contained within the first or the second polynucleotide.

Recombinases which may be employed include, but are not limited to, those of the Int family of recombinases, which consists of approximately 30 proteins which share an invariant pattern of four amino acids (Arg, His, Arg, Tyr), thought to reflect a common chemistry for the catalysis of DNA cleavage and ligation. (Landy, *Current Opinion in Genetics and Development*, Vol. 3, pgs. 699–707 (1993)). Examples of such recombinases include, but are not limited to, Cre recombinase and Flp recombinase.

In one embodiment, the recombinase is Cre recombinase, and the recombinase target sites contained in the first and second polynucleotides are Lox sites. Cre recombinase and its polynucleotide sequence, as well as the Lox site are found in bacteriophage P1, and are described further in Sternberg, et al., *J. Mol. Biol.*, Vol. 187, pgs. 197×212 (1986); Sauer, *Mol. Cell. Biol.*, Vol. 7, No. 8, pgs. 2087–2096 (June 1987); Sauer, et al., *Proc. Nat. Acad. Sci.*, Vol. 85, pgs. 5166–5170 (July 1988); Sauer, et al., *Nucleic Acids Research*, Vol. 17, No. 1, pgs. 147–161 (1989); and Sauer, *Meth. Enzymol.*, Vol. 225, pgs. 890–900 (1993).

In another embodiment, the recombinase is Flp recombinase and the recombinase target site is an frt site. Flp recombinase and its polynucleotide sequence, as well as the frt site, are described further in O'Gorman, et al., *Science*, Vol. 251, pgs. 1351–1355 (Mar. 15, 1991) and Golic, et al., *Cell*, Vol. 59, pgs. 499–509 (Nov. 3, 1989).

In a preferred embodiment, the recombinase target site of the first polynucleotide and the second polynucleotide are in the same orientation.

Although the scope of the present invention is not intended to be limited thereby, it is preferred that, in order to optimize the flexibility of removing adenoviral sequences from the first polynucleotide, which may be a plasmid, to design vectors which may include one or more of a variety of desired genes, the recombinase target site be located in the second polynucleotide near the ITR to be transferred. Thus, if one desires to transfer a 3' ITR with a terminal protein bound thereto from the second polynucleotide to the first polynucleotide, the recombinase target site in general is no more than 100 bases 5' from the 3' ITR of the second polynucleotide. If one desires to transfer a 5' ITR with a terminal protein attached thereto from the second polynucleotide to the first polynucleotide, the recombinase target site in general is located no more than 100 bases 3' to the 5' ITR located on the second polynucleotide.

As stated hereinabove, the first polynucleotide, in a preferred embodiment, is in the form of a plasmid. Preferably, prior to transfection of the plasmid into the cell, the plasmid is linearized. Thus, the plasmid, prior to linearization, may include a unique restriction site located between the ITR and the recombinase target site as hereinabove described.

In one embodiment, the plasmid is free of DNA expressing adenoviral proteins, and preferably also is free of DNA encoding selectable markers. Such a plasmid can accommodate large inserts (up to 37,200 base pairs) of DNA, which may include one or more DNA sequences encoding therapeutic agents as described hereinbelow. In such an embodiment, the second polynucleotide may be a helper virus including an adenoviral 5' ITR; an adenoviral packaging signal; DNA encoding adenoviral proteins for replication and packaging of the plasmid as an adenoviral vector particle; a recombinase target site; and an adenoviral 3' ITR. An adenoviral terminal protein is bound to at least the 5' ITR or 3' ITR which is to be transferred from the helper virus to the plasmid. When the plasmid and the helper virus are transfected into the cell along with the third polynucleotide including the DNA sequence encoding recombinase, there is generated a "gutless" adenoviral vector which includes an adenoviral 5' ITR; an adenoviral packaging signal; a DNA sequence encoding a heterologous protein; and an adenoviral 3' ITR. The vector is free of DNA encoding adenoviral proteins and preferably is free of DNA encoding a selectable marker. Also generated from the cell is the helper virus. In such a process, the helper virus remains at a level which is sufficient to support vector replication, yet at a low enough level whereby the plasmid-derived vector is not diluted out of virus preparations produced during a scale-up process. The adenoviral vectors generated from the plasmid may be separated or purified from the helper virus by conventional means such as equilibrium density centrifugation, which may be conducted, for example, on a CsCl gradient. In order to enable such separation, it is preferred that the adenoviral vector has a number of base pairs which is different from that of the helper virus. For example, the adenoviral vector has a number of base pairs which is less than that of the helper virus.

In one embodiment, the helper virus includes a mutated packaging signal. The term "mutated" as used herein, means that one or more base pairs of the packaging signal have been deleted or changed, whereby the helper virus is packaged less efficiently than wild-type adenovirus. The helper virus, which has a mutated packaging signal, is packaged less efficiently than the adenoviral vector (e.g., from about 10 to about 100 times less efficiently than the adenoviral vector).

Preferably, the packaging signal is mutated such that base pairs of the packaging signal are deleted. For example, when the adenoviral components of the polynucleotides are derived from Adenovirus 5 (ATCC No. VR-5), at least base pairs 267 to 358 are deleted from the packaging signal.

In another embodiment, the helper virus does not include DNA encoding the adenoviral E1a and E1b proteins, and the DNA encoding the adenoviral E1a and E1b proteins is provided by the cell.

In general, the first polynucleotide, which may be a plasmid, includes a sufficient number of base pairs to enable the generation of a mature adenoviral vector from such polynucleotide or plasmid. In one embodiment, the first polynucleotide or plasmid includes at least 25,000 base pairs, preferably from about 25,000 to about 37,200 base pairs. In addition to the adenoviral 5' ITR or 3' ITR, the packaging signal, the at least one DNA sequence encoding a heterologous protein, and the recombinase target site, DNA which may be included in the polynucleotide or plasmid, includes, but is not limited to, adenoviral DNA (such as, for example, the E1, E2, E3, E4, and/or the major late regions), and/or non-functional "stuffer" DNA sequences. In one embodiment, the at least one DNA sequence encoding a heterologous protein encodes a therapeutic agent. The term "therapeutic" is used in a generic sense and includes treating agents, prophylactic agents, and replacement agents.

DNA sequences encoding therapeutic agents which may be contained in the first polynucleotide, such as a plasmid as hereinabove described, from which the adenoviral vector is generated include, but are not limited to, DNA sequences encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; genes encoding GM-CSF; genes encoding ornithine transcarbamylase, or OTC; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; cytochrome b; glucocerebrosidase; T-cell receptors; the LDL receptor, ApoE, ApoC, ApoAI and other genes involved in cholesterol transport and metabolism; the alpha-1 antitrypsin (α1AT) gene; the insulin gene; the hypoxanthine phosphoribosyl transferase gene; negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper—zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthetase; vasoactive peptides; angiogenic peptides; the dopamine gene; the dystrophin gene; the β-globin gene; the α-globin gene; the HbA gene; protooncogenes such as the ras, src, and bcl genes; tumor-suppressor genes such as p53 and Rb; the LDL receptor; the heregulin-α protein gene, for treating breast, ovarian, gastric and endometrial cancers; monoclonal antibodies specific to epitopes contained within the β-chain of a T-cell antigen receptor; the multidrug resistance (MDR) gene; DNA sequences encoding ribozymes; antisense polynucleotides; genes encoding secretory peptides which act as competitive inhibitors of angiotensin converting enzyme, of vascular smooth muscle calcium channels, or of adrenergic receptors, and DNA sequences encoding enzymes which break down amyloid plaques within the central nervous system. It is to be understood, however, that the scope of the present invention is not to be limited to any particular therapeutic agent.

The DNA sequence (or transgene) which encodes the therapeutic agent may be genomic DNA or may be a cDNA sequence. The DNA sequence also may be the native DNA sequence or an allelic variant thereof. The term "allelic variant" as used herein means that the allelic variant is an alternative form of the native DNA sequence which may have a substitution, deletion, or addition of one or more nucleotides, which does not alter substantially the function of the encoded protein or polypeptide or fragment or derivative thereof. In one embodiment, the DNA sequence may further include a leader sequence or portion thereof, a secretory signal or portion thereof and/or may further include a trailer sequence or portion thereof.

The DNA sequence encoding at least one therapeutic agent is under the control of a suitable promoter. Suitable promoters which may be employed include, but are not limited to, adenoviral promoters, such as the adenoviral major late promoter; or heterologous promoters, such as the cytomegalovirus (CMV) promoter; the Rous Sarcoma Virus (RSV) promoter; inducible promoters, such as the MMT promoter, the metallothionein promoter; heat shock promoters; the albumin promoter; and the ApoAI promoter. It is to be understood, however, that the scope of the present invention is not to be limited to specific foreign genes or promoters.

The adenoviral components of the first polynucleotide, the second polynucleotide, and the DNA encoding proteins for replication and packaging of the adenoviral vector may be obtained from any adenoviral serotype, including but not limited to, Adenovirus 2, Adenovirus 3, Adenovirus 4, Adenovirus 5, Adenovirus 12, Adenovirus 40, Adenovirus 41, and bovine Adenovirus 3.

In one embodiment, the adenoviral components of the first polynucleotide are obtained or derived from Adenovirus 5, and the adenoviral components of the second polynucleotide, as well as the DNA sequences necessary for replication and packaging of the adenoviral vector, are obtained or derived from the Adenovirus 5 (ATCC No. VR-5) genome or the Adenovirus 5 E3-mutant Ad dl327 (Thimmapaya, et al., *Cell,* Vol. 31, pg. 543 (1983)).

Alternatively, the adenoviral vector may be generated by the use of purified recombinase protein in a cell-free system. In such an embodiment, the recombinase is not supplied by expression of the third polynucleotide hereinabove described. In this aspect of the present invention, the first polynucleotide and the second polynucleotide, as hereinabove described, are reacted with a recombinase in the absence of cells. By reacting the first and second polynucleotides with the recombinase, the recombinase interacts with the recombinase target sites in the first polynucleotide and in the second polynucleotide, whereby the recombinase (which may be selected from those hereinabove described) mediates sufficient site-specific intermolecular recombination to effect the transfer of an adenoviral ITR with a terminal protein bound to the ITR from the second polynucleotide to the first polynucleotide. The ITR, with the terminal protein bound thereto, serves as a template for replication of the first polynucleotide as an adenovirus, as hereinabove described. Once the polynucleotides have been reacted with the recombinase, the polynucleotides are transfected into cells which do not express a recombinase. Because recombination among at least a portion of the polynucleotides has occurred, whereby an ITR and terminal protein have been transferred from the second polynucleotide to the first polynucleotide as hereinabove described, adenoviral vector particles may be produced with great efficiency upon transfection of the first and second polynucleotides into the cells.

In one embodiment, the DNA encoding adenoviral proteins for replication and packaging of the first polynucleotide as an adenoviral vector particle is included in the second polynucleotide. In another embodiment, the DNA encoding adenoviral proteins for replication and packaging of the first polynucleotide as an adenoviral vector is included in the first polynucleotide.

In another embodiment, a portion of the DNA encoding adenoviral proteins for replication and packaging of the first polynucleotide as an adenoviral vector is included in the first polynucleotide, and a portion of the DNA encoding adenoviral proteins for replication and packaging of said first polynucleotide as an adenoviral vector is included in said second polynucleotide.

In a further embodiment, a portion of the DNA encoding adenoviral proteins for replication and packaging of the first polynucleotide as an adenoviral vector is independent of the first polynucleotide and the second polynucleotide, i.e., such portion of the DNA encoding adenoviral proteins for replication and packaging of the first polynucleotide as an adenoviral vector is contained in the cell prior to transfection of the cell with the first and second polynucleotides.

Once adenoviral vectors from the first polynucleotide are generated, such as, for example, from a plasmid, in accordance with the present invention, the adenoviral vectors may be employed in transfecting appropriate adenoviral packaging cell lines in order to produce more adenoviral vectors, which may be subjected to a variety of uses.

Uses of the adenoviral vectors of the present invention include the transduction of eukaryotic cells in vivo or in vitro as part of a gene therapy procedure, and the transduction of cells in vitro for the in vitro production of desired proteins or therapeutic agents.

In one embodiment, the adenoviral vectors are administered in vivo in an amount effective to provide a therapeutic effect in a host.

In one embodiment, the vector may be administered in an amount of from 1 plaque forming unit to about $10^{14}$ plaque forming units, preferably from about $10^6$ plaque forming units to about $10^{13}$ plaque forming units. The host may be a mammalian host, including human or non-human primate hosts.

The infectious adenoviral vectors are administered to the lung when a disease or disorder of the lung (such as, for example, cystic fibrosis) is to be treated. Such administration may be, for example, by aerosolized inhalation or brochoscopic instillation, or via intranasal or intratracheal instillation.

In another embodiment, the infectious adenoviral vectors are administered systemically, such as, for example, by intravenous administration (such as, for example, portal vein injection or peripheral vein injection), intramuscular administration, intraperitoneal administration, intratracheal administration, or intranasal administration.

The adenoviral vectors may be administered in combination with a pharmaceutically acceptable carrier suitable for administration to a patient. The carrier may be a liquid carrier (for example, a saline solution), or a solid carrier, such as, for example, microcarrier beads.

Cells which may be infected by the infectious adenoviral vectors include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; activated endothelial cells; epithelial cells; lung cells; keratinocytes; stem cells; hepatocytes, including hepatocyte precursor cells; fibroblasts; mesenchymal cells; mesothelial cells; parenchymal cells; vascular smooth muscle cells; brain cells and other neural cells; gut enterocytes; gut stem cells; and myoblasts.

The infected cells are useful in the treatment of a variety of diseases including but not limited to adenosine deaminase deficiency, sickle cell anemia, thalassemia, hemophilia A, hemophilia B, diabetes, α-antitrypsin deficiency, brain disorders such as Alzheimer's disease, phenylketonuria and other illnesses such as growth disorders and heart diseases, for example, those caused by alterations in the way cholesterol is metabolized and defects of the immune system.

In one embodiment, the adenoviral vectors may be used to infect lung cells, and such adenoviral vectors may include the CFTR gene, which is useful in the treatment of cystic fibrosis. In another embodiment, the adenoviral vector may include a gene(s) encoding a lung surfactant protein, such as SP-A, SP-B, or SP-C, whereby the adenoviral vector is employed to treat lung surfactant protein deficiency states.

In another embodiment, the adenoviral vectors may be used to infect liver cells, and such adenoviral vectors may include gene(s) encoding clotting factor(s), such as Factor VIII and Factor IX, which are useful in the treatment of hemophilia A and hemophilia B, respectively.

In another embodiment, the adenoviral vectors may be used to infect liver cells, and such adenoviral vectors may include gene(s) encoding polypeptides or proteins which are useful in prevention and therapy of an acquired or an inherited defect in hepatocyte (liver) function. For example, they can be used to correct an inherited deficiency of the low density lipoprotein (LDL) receptor, or a deficiency of ornithine transcarbamylase.

In another embodiment, the adenoviral vectors may be used to infect liver cells, whereby the adenoviral vectors include a gene encoding a therapeutic agent employed to treat acquired infectious diseases, such as diseases resulting from viral infection. For example, the infectious adenoviral vectors may be employed to treat viral hepatitis, particularly hepatitis B or non-A non-B hepatitis. For example, an infectious adenoviral vector containing a gene encoding an anti-sense gene could be employed to infect liver cells to inhibit viral replication. In this case, the infectious adenoviral vector, which includes a structural hepatitis gene in the reverse or opposite orientation, would be introduced into liver cells, resulting in production in the infected liver cells of an anti-sense gene capable of inactivating the hepatitis virus or its RNA transcripts. Alternatively, the liver cells may be infected with an infectious adenoviral vector which includes a gene which encodes a protein, such as, for example, α-interferon, which may confer resistance to the hepatitis virus.

In yet another embodiment, an adenoviral vector in accordance with the present invention may include a negative selective marker, or "suicide" gene, such as the Herpes Simplex Virus thymidine kinase (TK) gene. Such a vector may be employed in the treatment of tumors, including cancerous and non-malignant tumors, by administering the adenoviral vector to a patient, such as, for example, by direct injection of the adenoviral vector into the tumor, whereby the adenoviral vector transduces the tumor cells. After the cells are transduced with the adenoviral vector, an interaction agent, such as, for example, ganciclovir, is administered to the patient, whereby the transduced tumor cells are killed.

In another embodiment, the adenoviral vectors, which include at least one DNA sequence encoding a therapeutic agent, may be administered to an animal in order to use such animal as a model for studying a disease or disorder and the treatment thereof. For example, an adenoviral vector containing a DNA sequence encoding a therapeutic agent may be given to an animal which is deficient in such therapeutic agent. Subsequent to the administration of such vector containing the DNA sequence encoding the therapeutic agent, the animal is evaluated for expression of such therapeutic agent. From the results of such a study, one then may determine how such adenoviral vectors may be administered to human patients for the treatment of the disease or disorder associated with the deficiency of the therapeutic agent.

In another embodiment, the adenoviral vectors may be employed to infect eukaryotic cells in vitro. The eukaryotic cells may be those as hereinabove described. Such eukaryotic cells then may be administered to a host as part of a gene therapy procedure in amounts effective to produce a therapeutic effect in a host.

Alternatively, the vectors include a gene encoding a desired protein or therapeutic agent may be employed to infect a desired cell line in vitro, whereby the infected cells produce a desired protein or therapeutic agent in vitro.

The present invention may be employed in determining the minimum packaging requirements, in number of bases of DNA, for adenoviral vectors. Thus, polynucleotides such as plasmids may be constructed which have various lengths of DNA between the adenoviral ITR and the recombinase target site. Such plasmids then may be co-transfected with the third polynucleotide in accordance with the present invention, and generation of adenoviral vectors from each of these plasmids then may be determined. By determining which plasmids may be employed to generate adenoviral vectors, one may determine the minimum number of bases for generating an adenoviral vector from a plasmid including the components hereinabove described.

The present invention may be used to determine whether various adenoviral vector constructs will yield high titers of adenoviral vector. One may construct polynucleotides such as plasmids including an adenoviral ITR and a recombinase target site as hereinabove described, as well as various heterologous DNA sequences. Such plasmids may be transfected into recombinase expressing cells with the third polynucleotide as hereinabove described, and the titers of adenoviruses generated from the various plasmids then may be determined. From determining the various titers of adenovirus generated from the various plasmids, one can determine which heterologous DNA sequences do or do not affect the production of adenoviral vectors adversely.

The present invention also may be employed to develop adenoviral vectors which can be pseudotyped into capsid structures based on a variety of adenoviruses. Thus, one can use the adenoviral vectors generated in accordance with the present invention to generate adenoviral vectors having various capsids against which humans do not have, or rarely have, pre-existing antibodies.

For example, one may generate an adenoviral vector in accordance with the present invention from a plasmid having an ITR and a packaging signal obtained from Adenovirus 5, and a helper virus which contains adenoviral components obtained from the Adenovirus 5 genome. The viral vectors generated will have an Adenovirus 5 capsid. Adenovirus 5, however, is associated with the common cold, and anti-Adenovirus 5 antibodies are found in many humans. Thus, in order to decrease the possibility of the occurrence of an immune response against the adenoviral vector, the adenoviral vector having the Adenovirus 5 capsid, generated in accordance with the method of the present invention, may be transfected into an adenoviral packaging cell line which includes a helper virus which is a virus other than Adenovirus 5, such as Adenovirus 4, Adenovirus 12, or bovine adenovirus 3, or a derivative thereof. Thus, one generates a new adenoviral vector having a capsid which is not an Adenovirus 5 capsid, and therefore, such vector is less likely to be inactivated by an immune response. Alternatively, the vector may be transfected into an adenoviral packaging cell line which includes a helper virus including DNA encoding an altered Adenovirus 5 hexon, thereby generating a new adenoviral vector having an altered Adenovirus 5 capsid which is not recognized by anti-Adenovirus 5 antibodies. It is to be understood, however, that this embodiment is not to be limited to any specific pseudotyped adenovirus.

The present invention may be employed to provide an adenoviral vector based expression cloning system. Specifically, library sequences to be cloned may be ligated into the plasmid hereinabove described. The resultant plasmids then can be converted rapidly to an adenoviral cloning library which would mediate high level expression of the cloned sequences in vector-transduced target cells. The cells then may be screened for expression of the desired protein, and the vector could then be rescued from the cells with a helper virus.

In another aspect of the present invention, the heterologous DNA to be expressed includes DNA encoding a viral vector particle other than an adenoviral vector. Such DNA includes DNA sequences necessary for the production of viral particles (e.g., terminal repeat sequences, packaging signal, DNA encoding viral structural proteins), and DNA encoding a protein or polypeptide heterologous to the adenovirus and to the virus other than an adenovirus.

The DNA encoding the viral vector particle may be contained within the hereinabove described first polynucleotide.

Viral vector particles which may be encoded by the heterologous DNA include, but are not limited to, retroviral vector particles (including lentirvirus vector particles), adeno-associated viral vector particles, and alpha viral vector particles. Such viral vector particles also encode a heterologous protein or polypeptide, which may be selected from those hereinabove described.

In one embodiment, the viral vector particle is a retroviral vector particle. In such an embodiment, the heterologous DNA contained in the first polynucleotide includes the retroviral 5' LTR, the retroviral 3' LTR, a retroviral packaging signal, and a DNA sequence encoding a protein or polypeptide heterologous to adenovirus and retrovirus. The DNA sequence encoding the protein or polypeptide heterologous to adenovirus and retrovirus is flanked by the 5' LTR and packaging signal and the 3' LTR. The first polynucleotide also includes DNA encoding a retroviral gag protein, a retroviral pol protein, and a retroviral env protein and promoters controlling expression of the gag/pol and env DNA sequences. The promoters may be the constitutive or native gag/pol and env promoters, or may be tissue specific promoters, inducible promoters, or repressible promoters. The polynucleotides encoding the gag/pol and env proteins, and their promoters, are not flanked by the retroviral 5' and 3' LTR.

The first polynucleotide and the second polynucleotide are reacted with a recombinase. Such reaction takes place in a cell-free system as hereinabove described, or in a cell which includes a third polynucleotide which includes a DNA sequence encoding a site-specific recombinase, also as hereinabove described. The recombinase interacts with the recombinase target sites in the first polynucleotide and in the second polynucleotide to effect the transfer of an adenoviral ITR with a terminal protein bound to the ITR from the second polynucleotide to the first polynucleotide. The ITR with the terminal protein bound thereto serves as a template for replication of the first polynucleotide as an adenovirus. If the first and second polynucleotides were reacted with the recombinase in a cell-free system, the first and second polynucleotides, after reaction with the recombinase, are transfected into cells which will enable production of a hybrid adenoviral-retroviral vector, or HARV, from the first polynucleotide. If the first and second polynucleotides were transfected into a cell which includes a third polynucleotide including DNA sequence encoding a recombinase, the hybrid adenoviral-retroviral vector is produced by the cell from the first polynucleotide upon reaction of the first polynucleotide and the second polynucleotide with the recombinase expressed by the third polynucleotide.

In general, in the hybrid adenoviral-retroviral vector, or HARV, the adenoviral 5' ITR and the adenoviral 3' ITR flank the adenoviral packaging signal, the retroviral 5' LTR, the retroviral packaging signal, the DNA encoding a protein or polypeptide heterologous to adenovirus and retrovirus, the retroviral 3' LTR, the DNA sequence encoding a retroviral gag protein and a retroviral pol protein, and the DNA sequence encoding a retroviral env protein. The retroviral 5' LTR and the retroviral 3' LTR flank the retroviral packaging signal and the DNA encoding a protein or polypeptide heterologous to adenovirus and retrovirus. The DNA encoding a retroviral gag protein and a retrovral pol protein and the DNA encoding a retroviral env protein are not flanked by the retroviral 5' ITR and the retroviral 3' ITR. The adenoviral packaging signal is not flanked by the retroviral 5' LTR and the retroviral 3' LTR, and is located sufficiently proximal to one of the adenoviral 5' ITR or the adenoviral 3' ITR to enable the hybrid adenoviral-retroviral vector to be packaged.

The hybrid adenoviral-retroviral vector, or HARV, upon generation from the first polynucleotide, then is employed to transduce cells in vitro or in vivo. The transduced cells then secrete retroviral vectors including a polynucleotide encoding a heterologous protein or polypeptide. Thus, the transduced cells in effect become retroviral producer cells. The retroviral vectors then transduce nearby cells, whereby the polynucleotide encoding the heterologous protein or polypeptide is spread throughout cells of a desired tissue or organ, when the hybrid adenoviral-retroviral vector is administered in vivo. Transduction by the retroviral vectors results in integration of the polynucleotide encoding the heterologous protein or polypeptide into the cellular chromosomal DNA. Thus, a single administration of the hybrid adenoviral-retroviral vector results in high efficiency, permanent modification of desired cells, tissues, or organs.

In a preferred embodiment, the first polynucleotide includes a 5' adenoviral ITR and packaging signal and a retroviral vector construct containing the retroviral 5' and 3' LTR's, a retroviral packaging signal, and a polynucleotide encoding a heterologous polypeptide or protein. Located 3' to the 3' LTR are the retroviral gag/pol and env genes followed by a Lox site. The first polynucleotide, which may be in the form of a plasmid, is linearized and combined with a helper virus (i.e.,the second polynucleotide) in a reaction mixture with purified cre recombinase. The helper virus DNA is derived from Adenovirus 5, wherein the adenovirus E1 DNA sequence has been deleted and base pairs 267 to 358 of the packaging signal have been deleted. The helper virus DNA has a lox site upstream from its 3' ITR and has covalently attached adenoviral terminal proteins attached to the 5' ITR and the 3' ITR. The addition of the cre recombinase would convert some of the first polynucleotide into a replicatable hybrid adenoviral-retroviral vector. The first and second polynucleotides, after reaction with the cre recombinase, are co-transfected into a cell line that expresses the adenoviral E1 and E2a DNA sequences. This results in the generation of a hybrid adenoviral-retroviral vector that is devoid of all adenovirus backbone genes, along with a small amount of poorly packaged helper virus (due to the defective packaging signal in the helper virus). The hybrid adenoviral-retroviral vector then is purified from the helper by equilibrium density gradient centrifugation in CsCl. The hybrid adenoviral-retroviral vector then is used to transduce cells in vitro or in vivo. Cells which may be transduced include those hereinabove described. For example, the hybrid adenoviral-retroviral vectors may be administered by peripheral vein injection to transduce hepatocytes in vivo. The transduced cells then begin to produce retroviral vectors including a heterologous polynucleotide of interest, which may encode a therapeutic agent such as those hereinabove described. Such retroviral vectors then transduce nearby cells.

Retroviral vector sequences which may be included in the first polynucleotide include those known to those skilled in the art. The heterologous polypeptide may be transcribed from the LTR via an internal promoter. The sequences could encode for standard retroviral vectors or for self-inactivating or SIN vectors. The retroviral structural genes may be encoded by a single contiguous sequence, or may be encoded by separate sequences for gag/pol and env. The gag/pol and env genes could be controlled by constitutive promoters, tissue specific promoters, or inducible or repressible promoters. The use of tissue specific promoters limits retroviral vector production to a target tissue or organ. The use of an inducible or repressible promoters provides control over the rate at which cells transduced with the hybrid adenoviral-retroviral vector release the retroviral vector.

Because retroviral transduction requires cell division, in some instances it may be necessary to stimulate division of the cells of a tissue transduced with the hybrid adenoviral-retroviral vector. For example, cell division may be stimulated by administering to the host, along with the hybrid adenoviral-retroviral vector, an agent which stimulates cell division, such as a hormone or cytokine, including, but not limited to, keratinocyte growth factor for liver cells, and interleukins such as Interleukin-3 and Interleukin-6, or stem cell factor, for bone marrow cells. Alternatively, a polynucleotide encoding such hormone or cytokine may be included in the first polynucleotide, from which is generated the hybrid adenoviral-retroviral vector. Such a hybrid adenoviral-retroviral vector will secrete retroviral vectors and express the hormone or cytokine which stimulates cell division.

Alternatively, a CTL response against the retroviral packaging proteins (i.e., gag/pol and env) expressed in the cells transduced initially with the hybrid adenoviral-retroviral vector would eliminate such cells. The elimination of such cells may stimulate a cell turnover which permits retroviral transduction.

When the transduced cells are contained in organs of juvenile or adolescent animals, such cells may be growing at a rate that obviates the need for additional stimulation of cell division.

In certain instances, such as, for example, the treatment of tumors, the stimulation of cell division is not necessary in that the cells are dividing. In such cases, the hybrid adenoviral-retroviral vector may be administered to the cells without concurrent stimulation of cell division.

When the hybrid adenoviral-retroviral vector includes retroviral sequences derived from a lentivirus, the stimulation of cell division is not necessary because lentiviral vectors can transduce non-dividing cells.

Advantages of this aspect of the present invention include the ability to obtain high efficiency, permanent genetic modification of a desired tissue or organ with a single administration of the hybrid adenoviral-retroviral vector. This aspect of the present invention also takes advantage of the ability of a "gutless" adenoviral vector to encode large and multiple transgenes. This enables the retroviral vector sequences and the retroviral packaging sequences to be included in the same vector.

Another advantage of this aspect of the present invention is that it enables a transgene to be spread throughout a tissue or organ. The constant secretion of a retroviral vector from the transduced target cells fosters spread of the heterologous gene. The hybrid adenoviral-retroviral vector can be used to transduce cells in a large variety of target organs (such as, for example, liver), and transduction can be uniform throughout an organ. In addition, there is no injection of foreign cells, the retroviral vectors are produced by the host animal's own cells, and a large percentage of cells in a tissue or organ can be converted into retroviral vector producer cells.

Furthermore, the spread of retroviral vectors throughout a tissue or organ can occur without the need for the retroviral vectors to enter the circulation. Even if the retroviral vectors are exposed to plasma in a human, the retroviral vectors may be complement resistant because they were produced in human cells.

In accordance with another aspect of the present invention, the introduction of retroviral vectors into cells may be achieved using a first adenoviral vector and a second adenoviral vector. The first adenoviral vector includes DNA encoding a retroviral 5' LTR, a retroviral packaging signal, DNA encoding at least one heterologous protein or polypeptide, such as those hereinabove described, and a retroviral 3' LTR. The second adenoviral vector includes DNA encoding the retroviral gag/pol and env proteins and promoters controlling the DNA sequences encoding the gag/pol and env proteins.

The first and second adenoviral vectors each may be generated from a first polynucleotide according to the methods hereinabove described. Other examples of the first and second adenoviral vectors which may be modified to contain the retroviral vector and retroviral structural protein sequences include, but are not limited to, those described in PCT Application No. WO94/23482, published Oct. 27, 1994; PCT Application No. WO96/18418, published Jun. 20, 1996; and U.S. Pat. No. 5,543,328, the contents of which are incorporated herein by reference.

Upon transduction of cells in vivo or in vitro with the first and second adenoviral vectors, the cells will secrete retroviral vectors which will transduce nearby cells, thereby engineering such cells with a polynucleotide encoding at least one heterologous protein or polypeptide.

EXAMPLES

The invention now will be described with respect to the following examples; however, the scope of the present invention is not intended to be limited thereby.

Example 1

Generation of Plasmid Which Expresses Cre Recombinase

Plasmid pGRE5-2/EBV (United States Biochemical, Cleveland, Ohio) (Mader, et al., *Proc. Nat. Acad. Sci.*, Vol. 90, pgs. 5603–5607 (1993)) was employed as a backbone plasmid for construction of a plasmid which includes the DNA sequence encoding Cre protein under the control of the GREW5 promoter. The Cre protein DNA sequence was obtained from plasmid pBS353, obtained from Brian Sauer, National Institutes of Health, Bethesda, Md. The Cre protein DNA sequence was excised from plasmid pBS353 as a KpnI fragment and inserted into pGRE5-2/EBV opened with KpnI. The resulting plasmid, pGreCre, contained the dexamethasone inducible GREW5 promoter, a short length of sequence from the adenovirus major late promoter and transcript, an intron, the Cre coding sequence, and a polyadenylation signal. pGreCre also contains EBNA1 and OriP, to enable episomal propagation in eukaryotic cells, as well as a hygromycin resistance gene. pGreCre was transfected into 293-EBNA cells (Invitrogen Corporation, San Diego, Calif.), hereinafter referred to as 293e cells, and the cells then were selected with hygromycin. Clones containing the plasmid were screened for plasmid copy number by Southern Blot analysis. It is expected that the magnitude of Cre protein expression correlates with the episomal plasmid copy number. Clones 1 and 26 were selected for further experimentation.

Example 2

In order to verify that efficient Cre-mediated recombination would occur in the two clones mentioned in Example 1, a plasmid known as pBS375, provided by Dr. Brian Sauer, which contains two Lox sites was transfected into the cells. After 2 and 4 days, DNA was obtained from the cells, and the percentage of recombined versus unrecombined plasmid was determined by Southern Blot analysis (FIG. 1). After 4 days, more than 90% of the plasmid had been recombined despite the fact that there were many plasmid copies in each cell, indicating the Cre protein-mediated recombination was very efficient.

Example 3

Generation of Ad-dl327-Derived Vector Having a Lox Site in its Right End

Figure 3:
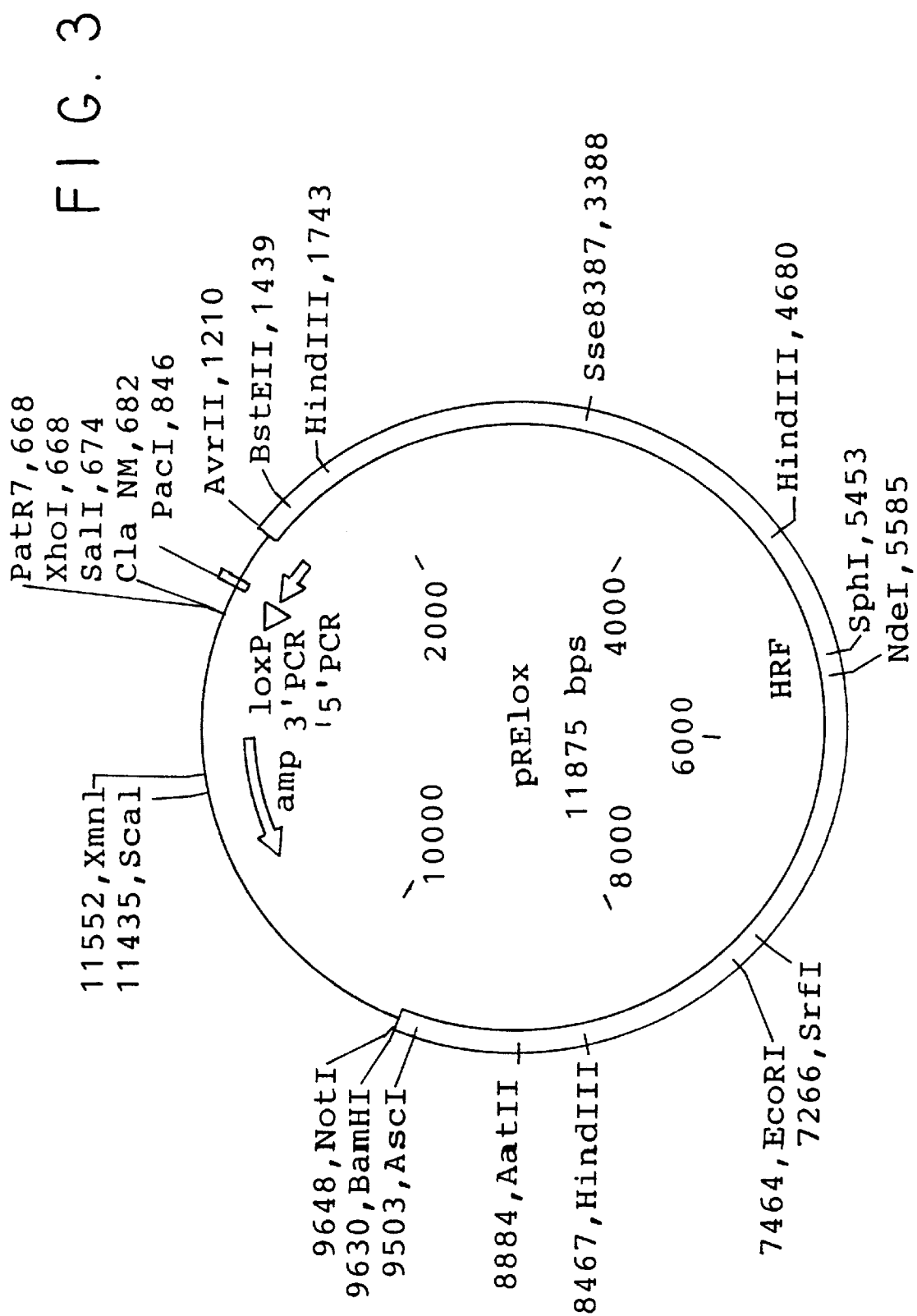
FIG. 3 is a map of plasmid pRElox.

Previous adenoviral literature indicates that nearly all of the base pairs of the far right end of the virus are important for normal function of the E4 promoter; however, there was a short region just upstream from the right ITR which had not been implicated in the function of this promoter. This region contained the sequence TTAA. (FIG. 2). Through a series of constructions, the right end of the adenoviral (Adenovirus 5) sequence was incorporated into a pBR322 plasmid backbone and an additional TTAA sequence was inserted next to the TTAA sequence described above. The resulting sequence, TTAATTAA placed a unique PacI site approximately 50 bp upstream from the right ITR. A 34 base pair Lox site then was inserted into this PacI site. Through several more constructions, additional upstream adenoviral sequences were incorporated to generate the plasmids pRElox (FIG. 3) and pBRAD (FIG. 4). pRElox was used to generate the adenovirus DL327Lox (a DL327 derivative containing the Lox site approximately 50 bp upstream from the 3' ITR), and pBRAD was used to generate the plasmid pVN (See Example 4 below). The details of these constructions are as follows:

1. PCR of 151 bp of Left End of Ad dl327 (bp33906–34057)
    Oligomers used were
    1. SZR 31-5' GGTTAA-TTA AGA AAA CTA CAA TTC CCA (SEQ ID NO:1) and
    2. MJK 2-5' GTGGGATC-CAT CAT CAA TAA TAT ACC TTA TTT TGG A (SEQ ID NO:2)

[The sequences before the hyphen in SZR 31 and MJK 2 (above) are not present in the adenovirus 5 sequence. The leader in MJK 2 allows the PCR product to be cut with BamHI (recognition sequence-GGATCC). The leader in SZR 31 allows the PCR product to be cut with PacI (recognition sequence-TTAATTAA)].

The PCR was carried out using Ad5 dl327 as substrate and the 158 bp product was digested with BamHI and cloned in between the BamHI and EcoRV sites of pBluescript II SK (+) (from Stratagene, LaJolla, Calif., hereinafter referred to as pBS). This clone is called pBS3' pcr.

2. PCR of 763 bp of Ad dl327 (bp33141–33905) Upstream of Last 151 bp
    Oligomers used were
    1. SZR 35-5' TAA GCT CCG GAA CCA CCA CAG and
    2. SZR 30-5' GGTTAA-TTA AAA TGG GAA GTG ACG TAA CGT G (SEQ ID NO:4) [The sequence before the hyphen allows the product to be cut with PacI.]

The PCR was carried out using Ad dl327 as substrate and the 763 bp product was digested with XmaI and the resulting 437 bp fragment was cloned in between the XmaI and EcoRV sites of pBluescript II SK (+). This clone is called pBS5' pcr.

3. Combining the Two PCR Fragments Using the PacI Site
    Both PCR fragments contain a novel PacI site generated as a result of the extra bases present on the primers SZR 31 and SZR 30. This site was used to join the two as follows: The plasmid pBS3' pcr was cut with BamHI, filled in with Klenow and then cut with PacI. The 155 bp 3' PCR fragment was then ligated into the plasmid pBS5' pcr which had been cut with HindIII, filled in with Klenow and then cut with PacI. The resulting plasmid, pBSpac, contains all of the Ad5 sequences to the right of the XmaI site (located on bp 33475 on the Ad dl327 genome) with an insertion of four additional bases (TTAA) at a site corresponding to bp #33905 of the dl327 genome. This generates a PacI site at this position.

4. Cloning Additional Sequences From Right End of Ad5
    Ad5 dl327 was cut with SnaBI (bp#25171) and AvrII (bp#33585) and the 8414 bp fragment was ligated into pBSpac digested with AvrII and SmaI. This plasmid is called pREpac 5. Insertion of the loxP Sequence into the PacI Site of pREpac
    Two oligomers
    SZR 36 (5'-ATA ACT TCG TAT AAT GTA TGC TAT ACG AAG TTA TTT AAT) (SEQ ID NO;5) AND
    SZR 37 (5'-TAA ATA ACT TCG TAT AGC ATA CAT TAT ACG AAG TTA TAT) (SEQ ID NO:6)
    were annealed to generate the loxP sequence flanked by PacI cohesive ends. This was ligated into pREpac linearized with PacI. The resulting plasmid, where the orientation of insertion of loxP (as defined by B. Sauer, *Methods in Enzymology*, volume 225, pgs. 890–900) was left to right (with respect to adenoviral sequences), was chosen. This plasmid, pRElox (FIG. 3), has a single PacI site following the loxP sequence.

Figure 4:
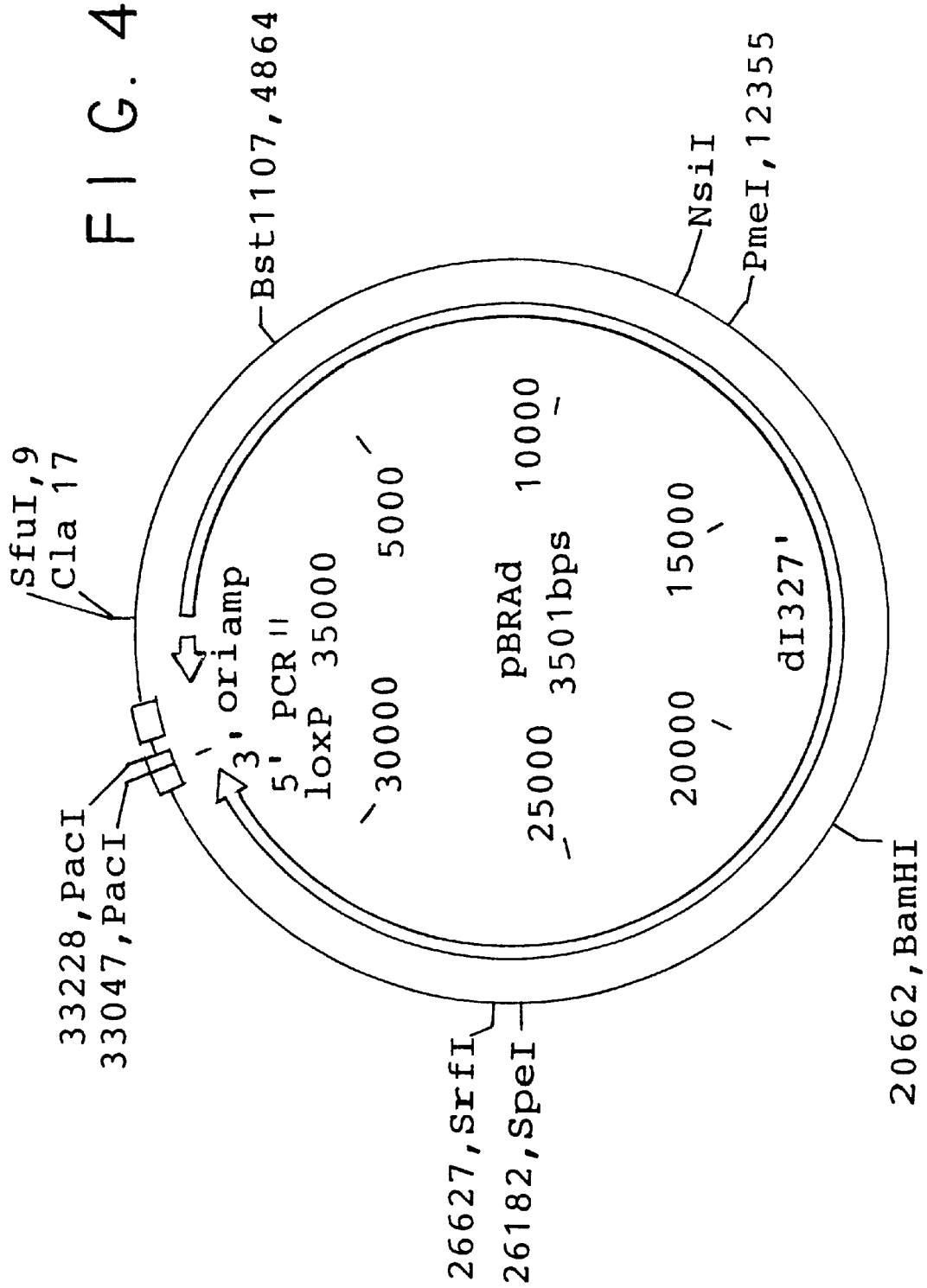
FIG. 4 is a map of plasmid pBRAD.

6. Construction of pBRAd—a Plasmid Containing the 33,140 bp of Ad dl327 Sequence to the Right of the ClaI Site at bp # 917 and Also Harboring a loxP Sequence Near the right End as Described Above in the Construction of pRElox
    This was done in two steps:
    (i) The right end of Ad5 present in pRElox was excised using ClaI and BamHI and this 8945 bp fragment was ligated into pBRL between its AccI and BamHI sites. This plasmid is pBRE. (The plasmid PBRL is a derivative of the plasmid pBR322 where the tetracycline resistance gene has been removed and replaced by a cloning polylinker.)
    (ii) The plasmid pBRE was digested with SpeI and ClaI and the resulting 9133 bp fragment was ligated to a 26,165 bp fragment derived from Ad dl327 digested with the same two enzymes. This plasmid is pBRAd (FIG. 4).

7. Construction of an Ad dl327 Derivative Containing the loxP Sequence Near its Right End
    Ad dl327 DNA was cut with EcoRI and the resulting 27,331 bp left end of the viral DNA was ligated to pRElox linearized with EcoRI. The ligation mixture was used to transfect 293 cells using the calcium phosphate procedure. Plaques obtained after 14 days were picked up and propagated. The plaques were screened for the presence of Ad-dl327 that incorporated a Lox site in its far right end. The new virus, DL327Lox, a schematic of which is shown in FIG. 2, then was amplified into a large preparation on 293 cells. DNA with terminal proteins intact then was obtained from this viral preparation using a guanidinium lysis procedure. This procedure purifies virus by equilibrium banding in CsCl, and includes extensive dialysis versus TE (10 mM Tris, pH 8.0; 1 mM EDTA) to remove CsCl. This procedure was obtained from Dr. Gary Ketner, Johns Hopkins University, Baltimore, Md.). The procedure was carried out as follows:
    For a virus volume of X ml in TE, X ml of 8M guanidinium hydrochloride (GuHCl) is added, followed by the addition of phenylmethylsulfonylfluoride (0.1M in ethyl alcohol) to 1 mM. The mixture is mixed gently and incubated on ice for 5 minutes. 4× ml of 4MGuHCl and 4.539M CsCl (76.49 g/100 ml) are added. The final CsCl concentration is 3.026M. The mixture is spun in a Sorvall TV865 vertical rotor or equivalent at 45,000 rpm overnight. The bottom of the centrifuge tube is pierced and fractions of about 0.25 ml are collected. DNA is found by measuring the $A_{260}$ of each fraction. The fraction containing DNA is dialyzed against TE. This DNA with terminal proteins intact served as the helper DNA in subsequent experiments.

Example 4

Figure 5:
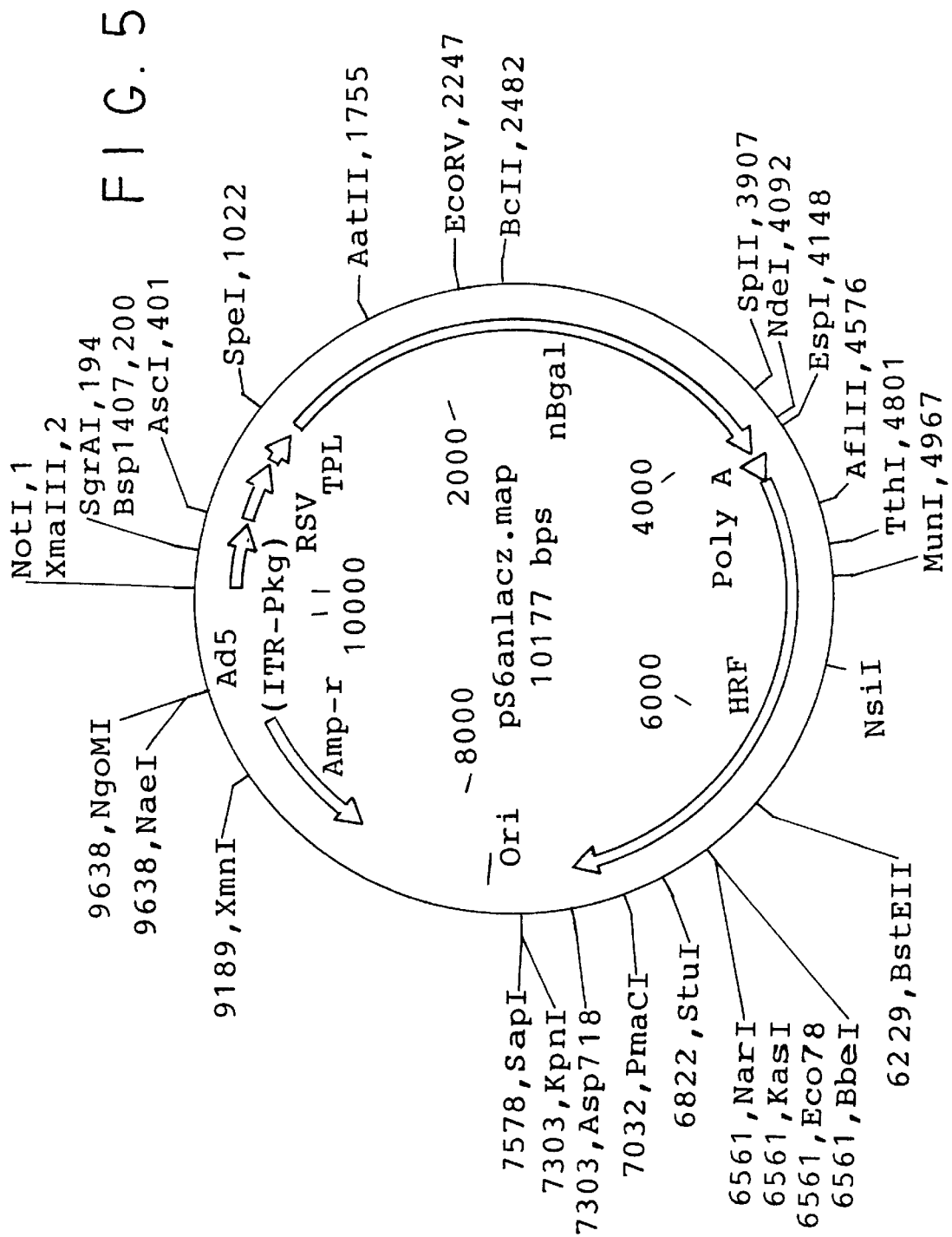
FIG. 5 is a map of plasmid pS6ANLacZ.
Figure 6:
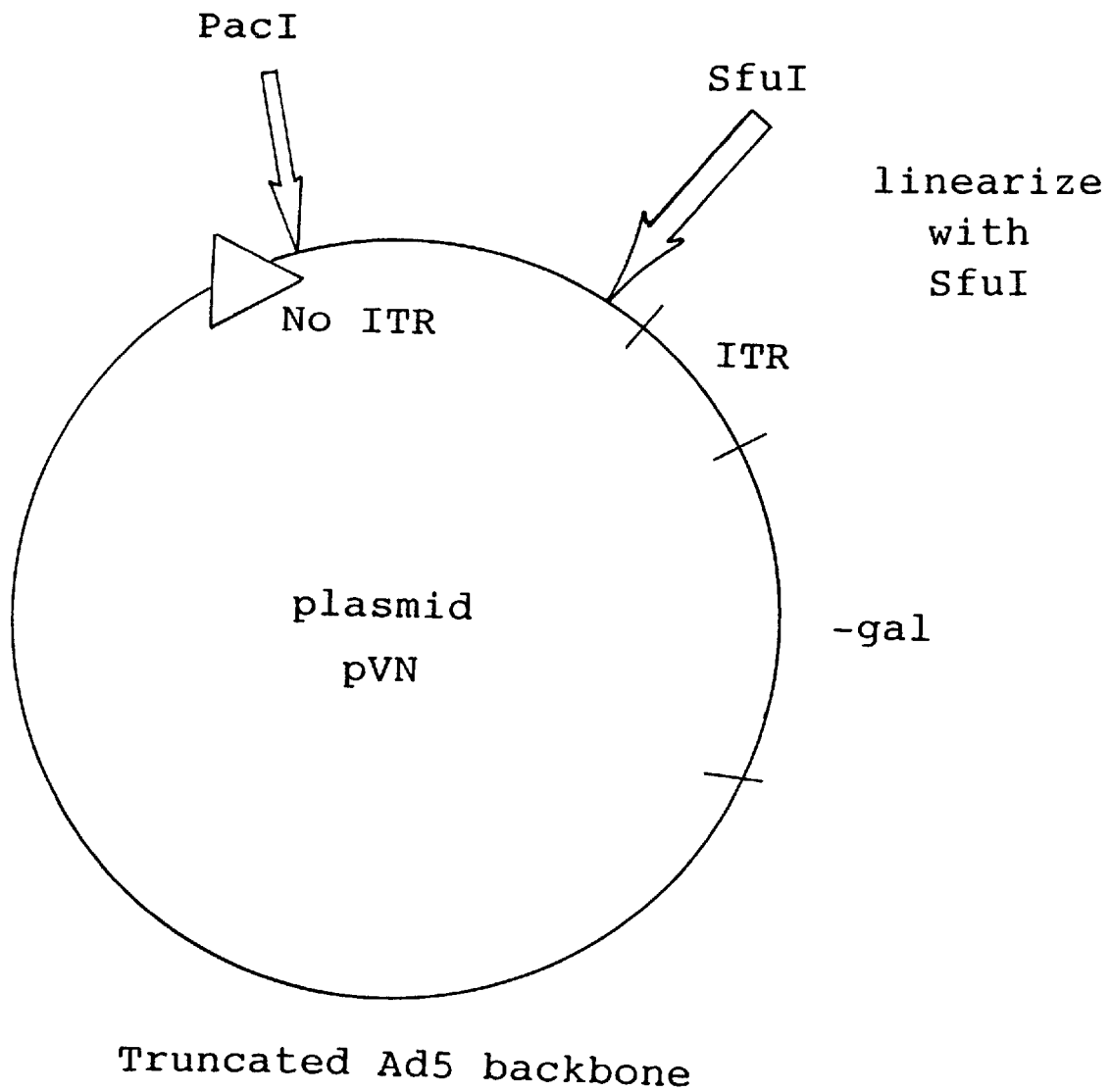
FIG. 6 is a map of plasmid pVN.

Generation of Plasmid Including a β-galactosidase Gene, a Left ITR and a Right Lox Site The starting plasmid in this example is pBRAD (FIG. 4) which was described in Example 3 above. Because pBRAD and DL327Lox both were derived from the same precursor plasmid, pRElox (FIG. 3), the two have identical sequences in the region of the 3' ITR and Lox site. The right ITR in pBRAD was removed by digestion with PacI followed by re-ligation. (There were PacI sites on either side of the ITR.) Next, the left most 11,000 bp of the adenoviral sequences were removed by digestion with SfuI and NsiI. In their place was inserted an ITR/β-galactosidase expression sequence taken from the shuttle vector pS6ANLacZ. (FIG. 5.)

pS6ANLacZ is derived from pAvS6-nLacZ (described in published PCT Application No. WO95/09654, published Apr. 13, 1995), wherein an ATG codon immediately 5' the adenoviral 5' tripartite leader sequence was removed by digestion with SfiI, removal of the 3' overhang with T4 polymerase, and religation. pS6ANLacZ is cut with NotI and NsiI to obtain the ITR/β-galactosidase expression sequence. An SfuI linker then is placed at the NotI site, and the ITR/β-galactosidase expression sequence is ligated to the SfuI/NsiI digested pBRAD. This yielded pVN (FIG. 6), which contains in a pBR322 backbone, a left ITR, an adenoviral packaging sequence, an RSV promoted β-galactosidase expression cassette, a short sequence of adenoviral sequences from the left end of the virus, the right two-thirds of Adenovirus 5 (without a right ITR), and a Lox site in the same orientation as the Lox site in DL327Lox.

Example 5

Generation of a pVN Derived Vector

A schematic of the generation of an adenoviral vector from pVN is shown in FIG. 7.

Figure 8C:
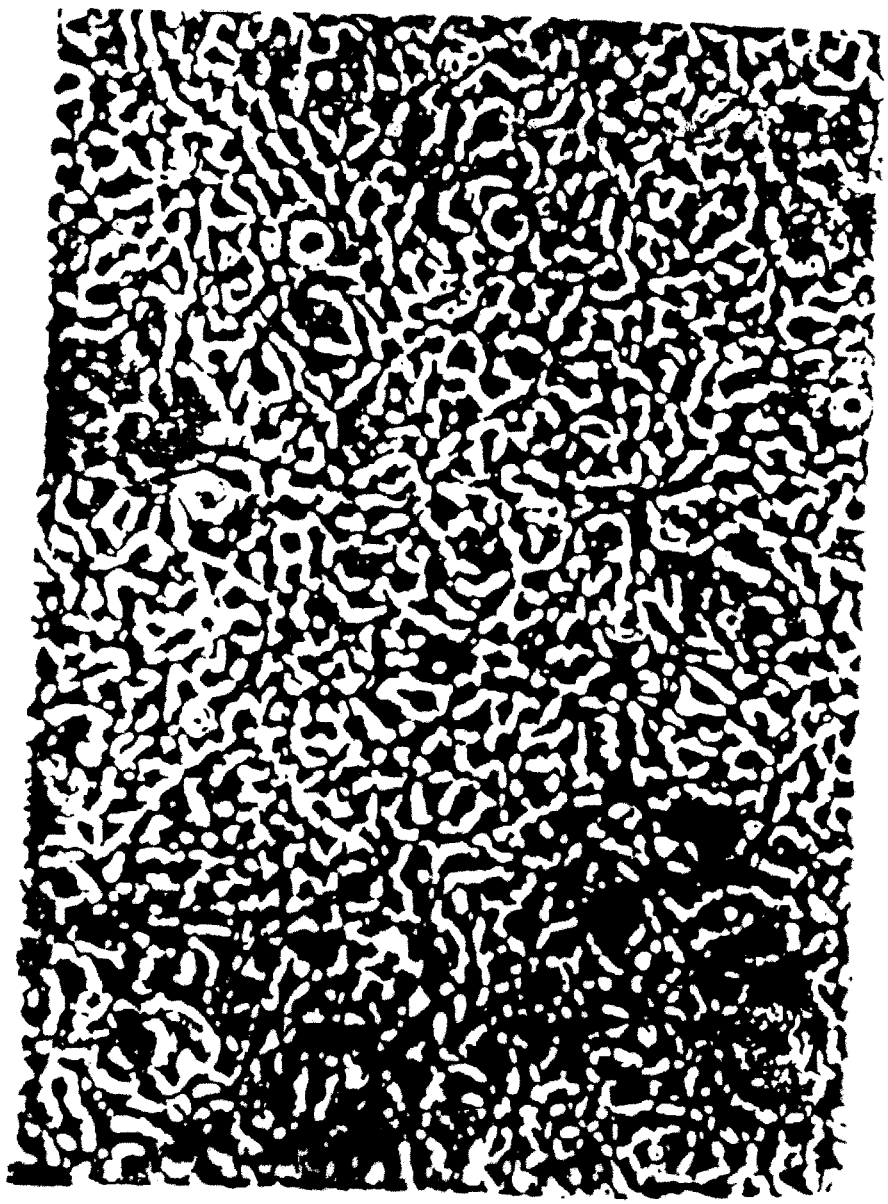
FIG. 8 depicts the results of X-gal staining of 293 cells contacted with viral lysate from 293e Cre cells transfected with pVN and DL327Lox, of 293 cells contacted with viral lysate from 293e Cre cells transfected with DL327Lox alone, and of 293 cells contacted with viral lysate from 293e Cre cells transfected with pVN alone.

6 µg of DNA with terminal proteins intact obtained from DL327Lox were co-transfected with 6 µg of SfuI linearized pVN plasmid into 293eCre clone 26 cells on a 6 cm dish. In these cells, Cre protein expression is controlled by a dexamethasone inducible promoter. Thus, dexamethasone was added to the tissue culture medium to insure maximal induction of Cre protein expression. Three days later, virus had spread through the monolayer and cytopathic effects were evident. The cells were harvested and a crude viral lysate was prepared by 5 freeze/thaw cycles. The lysate was cleared with low speed centrifugation and 50 µl or 250 µl of supernatant was used to infect monolayers of 293 cells. The following day, cytopathic effects were evident in these 293 cells and they were stained with X-gal. One-third of the cells in each case stained blue, thus indicating that a substantial fraction of the viral particles coming from the original transfection contained the β-galactosidase vector derived from the pVN plasmid. (See FIG. 8.) It is noteworthy that this vector is devoid of most of the first 11,000 bp of Adenovirus 5, including the E1 and E2B sequences, the major late promoter, and the 5' sequences of the major late transcript. Control transfections were done with DL327Lox DNA alone and pVN alone. No β-galactosidase vector was obtained with either control.

From the above experiment, it is concluded that the use of Cre recombinase enables the rapid generation of an adenoviral vector without the need to obtain, screen, and expand plaques.

Example 6

In another experiment, designed to scale up the production of the β-galactosidase vector, 500 µl of crude viral lysate obtained from the transfected cells in Example 5 were applied to 293 cells on a 15 cm tissue culture dish. Two days later, cytopathic effects were evident in these 293 cells. A crude viral lysate was prepared by 5 cycles of freeze/thawing, and the lysate was used to infect twenty 15 cm dishes of 293 cells. One day later, cytopathic effects were evident and X-gal staining of one plate indicated that one quarter of the cells contained plasmid-derived B-gal vector. The following day the cytopathic effects were complete and the cells were harvested. The lysate prepared from these cells is processed with standard adenovirus preparation techniques: a CsCl step gradient followed by an overnight continuous CsCl gradient. The continuous gradient yields a strong band of DL327Lox virus and a smaller upper band of B-gal vector. The B-gal vector is removed from the centrifuge tube and its titer is determined by infecting 293 cells and staining with X-gal the following day. The B-gal vector is subjected to a second scaleup procedure in which 293 cells are co-infected with B-gal vector at a multiplicity of infection of approximately two and DL327 at a multiplicity of infection of approximately 1. B-gal vector prepared from lysates of these cells is purified by centrifugation as above. This procedure yields high titer, plasmid-derived, B-gal vector.

Example 7

In this example, the efficacy of using Cre recombinase to generate a vector which is devoid completely of adenoviral backbone genes was demonstrated. The remainder of the adenoviral open reading frames were removed from the plasmid pVN and replaced with sequences from bacteriophage lambda. These sequences were chosen because they would not be expected to express proteins in eukaryotic cells and they provide length and that is believed to be necessary for efficient vector production.

Figure 9:
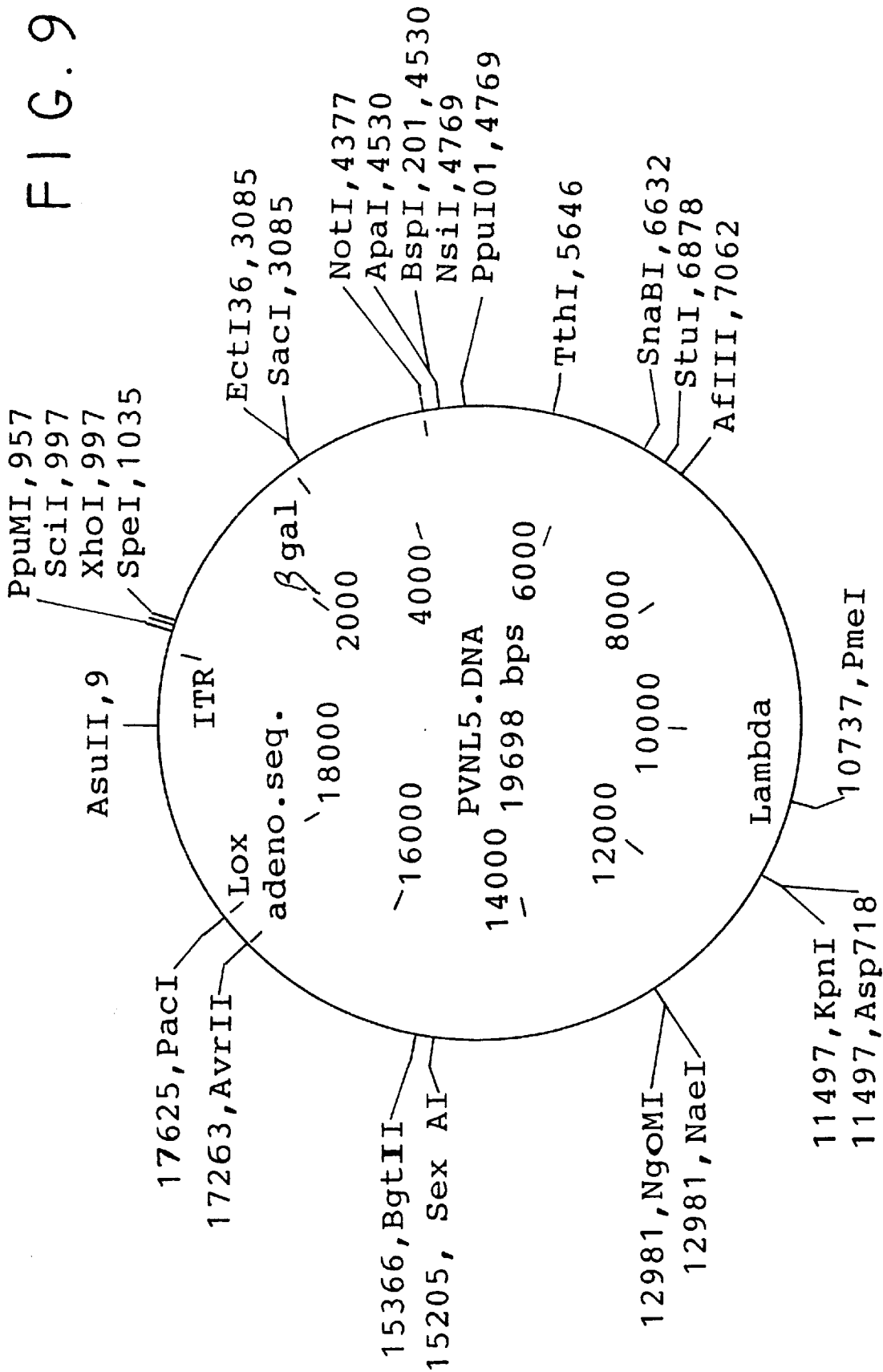
FIG. 9 is a map of plasmid pVNL5.

Several construction steps were involved. The adenoviral genes were removed from pVN by digestion with AflII and AvrII and a NotI linker was placed at the AflII site. A sequence from bacteriophage lambda from bp 9941 to a naturally occurring AvrII site at 24322 was ligated into the pVN backbone, NotI to AvrII, to yield the plasmid pVNL3. This plasmid contains the left ITR, adenoviral packaging signal, RSV promoted beta-galactosidase gene, SV40 polyadenylation signal, a small stretch of Ad5 sequence (from Ad5 bp 3328–3533), bacteriophage lambda sequence, 324 bp of Ad5 sequence from the right end of Ad5 (Ad5 bp 35463–35786), and the lox recombination site immediately upstream from the PacI site. This plasmid also contained an SfuI site upstream from the ITR to be used for linearization. This site, however, was not unique and also was present at bp 12,709. To remove the second SfuI site, pVNL3 was digested with KpnI (which flanked the SfuI site) and religated to yield plasmid pVNL4. The next construction was designed to remove the small stretch of adenoviral sequence just upstream from the NotI site. pVNL4 was digested with SacI and NotI which removed the end of the beta-galactosidase sequence, SV40 polyadenylation signal, and the adenoviral sequence. This region was replaced by a sequence, also from pVNL4, from SacI to BamHI with a NotI linker appended to the BamHI site. This fragment contained the end of the beta-galactosidase sequence and the SV40 polyadenylation signal. The plasmid was termed, pVNL5 (FIG. 9), and the only Ad5 sequences it encoded were the left ITR, packaging signal, and the 324 bp from the right end. This plasmid did not encode any adenoviral proteins.

Figure 10:
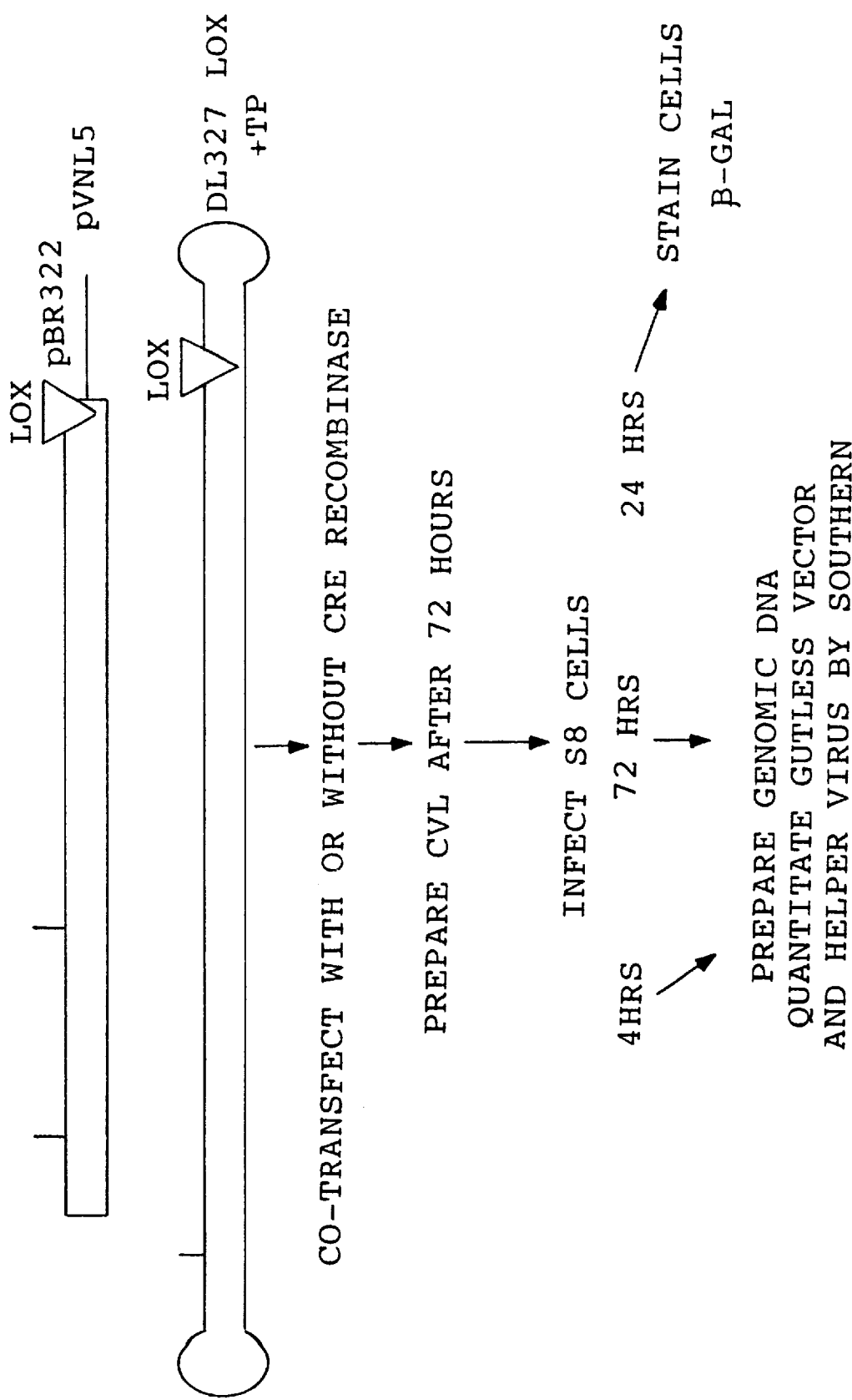
FIG. 10 is a schematic of the generation of adenoviral vectors from pVNL5 and Ad dl327lox, and the transduction of such adenoviral vectors into AE1-2A.S8 cells.

To demonstrate that Cre-mediated recombination greatly improved the efficiency of generating an adenoviral vector (and in this case, an adenoviral vector devoid of adenoviral backbone genes), the following experiment was performed as outlined schematically in FIG. 10. 6 $\mu$g of SfuI-linearized pVNL5 was mixed with 6 $\mu$g of DNA with terminal proteins intact derived from DL327Lox. The mixture then was transfected into 293eCre cells (which express Cre recombinase). Alternatively, the Cre-medicated recombination was performed in a cell-free system. 1.2 $\mu$g of the linearized pVNL5 mixed with 2.1 $\mu$g of the DL327Lox DNA with terminal proteins intact were reacted with a 25 fold molar excess of Cre protein in a 30 $\mu$l reaction mixture according to the procedure of Sauer, *Methods in Enzymology,* Vol. 225, pg.890 (1993) with the exception the reaction was not stopped by heating. Subsequent restriction diagnostics on the reaction mix demonstrated that approximately 10–20% of the reactants had undergone recombination. The reaction mixture then was transfected into 293e cells (that do not express Cre) and 293eCre cells (that do express Cre).

Figure 11:
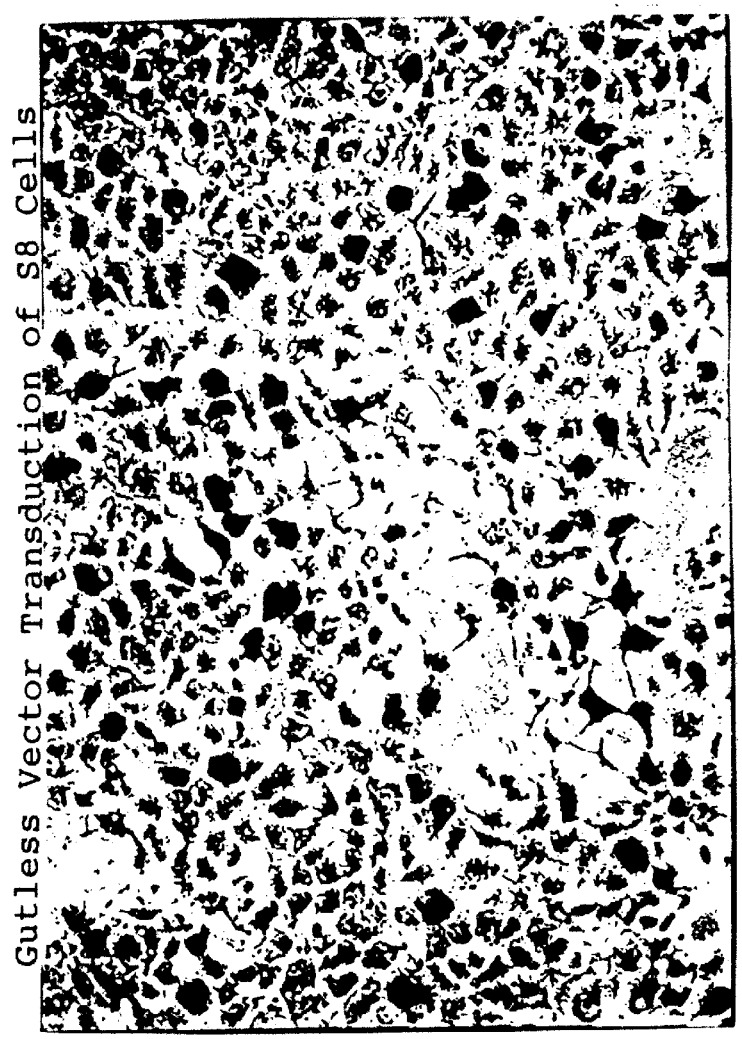
FIG. 11 shows X-gal stained AE1-2A.S8 cells transduced with a crude viral lysate generated from transfection of a cell-free cre/lox recombination of pVNL5 and Ad dl327lox with terminal protein.

72 hours later the transfected cells were harvested and a crude viral lysate (CVL) was prepared by 5 freeze/thaw cycles and low speed centrifugation to remove the cell debris. One tenth of each CVL was used to transduce AE1-2A.S8 cells (Gorziglia, et al., *J. Virol.,* Vol. 70, No. 6, pgs. 4173–4178 (June 1996) and the following day the cells were stained with X-gal for beta-galactosidase expression. In each case where the two DNA reactants had been exposed to Cre, either intracellularly, in a cell free reaction, or both, the CVL contained vector that expressed beta-galactosidase in the transduced AE1-2A.S8 cells. FIG. 11 is an example of X-gal stained cells that had been transduced with CVL from 293e cells transfected with DNA that had been exposed to Cre in a cell free reaction. Control cohorts in which the Cre was omitted revealed substantially fewer blue staining cells. Thus, Cre-mediated recombination improved the efficiency with which an adenoviral vector (devoid of any adenoviral backbone genes) was derived from a transfection.

Figure 12:
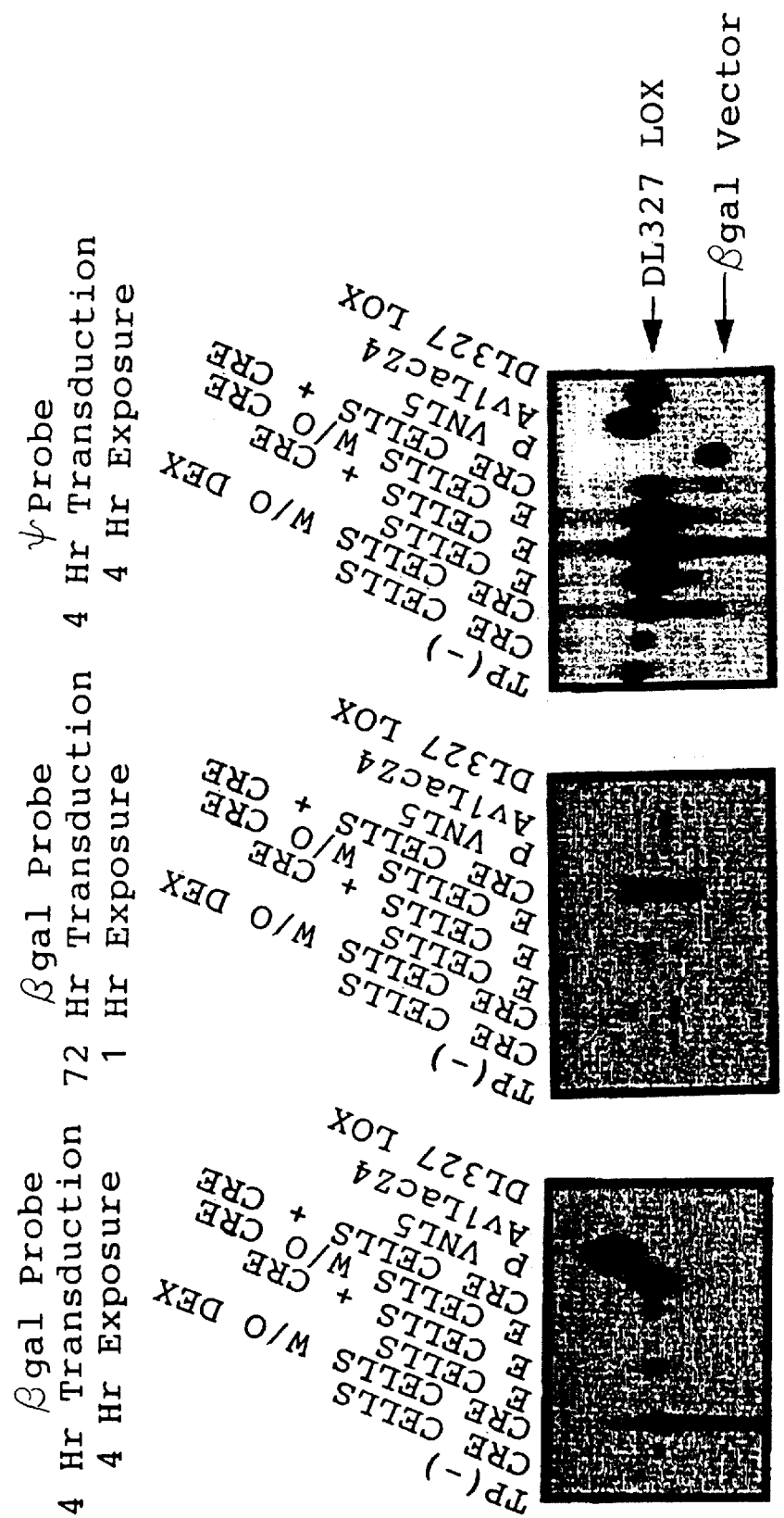
FIG. 12 shows Southern blots of genomic DNA from AE1-2A.S8 cells that were contacted with crude viral lysate including adenoviral vectors generated as a result of creme-diated recombination between pVNL5 and Ad dl327lox.

To quantitate further the effectiveness of Cre for generating rapidly an adenoviral vector and to verify the structure of the vector, CVL-transduced AE1-2A.S8 cells were analyzed by Southern analyses as follows. One quarter of each CVL above was used to transduce AE1-2AS8 cells. At 4 and 72 hours later, genomic DNA was prepared from the cells, digested with PmeI, and subjected to Southern analyses. Two probes were used, one which hybridized only to the beta-galactosidase gene (which detects only the vector DNA) and one which hybridized to the packaging signal (which detects both the vector and DL327Lox DNA). The results are shown in FIG. 12. The left panel is a Southern analysis with the $\beta$-galactosidase probe performed on genomic DNA from AE1-2A.S8 cells transduced with CVLs for only four hours. The bands represent the vector that was in the CVLs and that transduced the AE1-2A.S8 cells. In each case in which Cre recombinase was present, a strong band is seen. This was true when Cre was used intracellularly (lanes 2 and 3), or in a cell-free reaction (lane 5), or both (lane 7). In the absence of Cre (lanes 4 and 6) bands were faint or undetectable. Lanes 8–10 were control lanes which demonstrated the sensitivity and specificity of the beta-galactosidase probe. They contained pVNL5 plasmid, DNA derived from Av1LacZ4 (a standard beta-galactosidase adenoviral vector), and DNA derived from Ad dl327. The presence of a band in every case in which Cre was used and the absence of a band in each case where Cre was omitted again demonstrates that Cre-mediated recombination dramatically improves the efficiency with which adenoviral vectors, and in particular vectors without backbone genes, can be generated.

To verify further that the bands in the Southern blot hereinabove described represented transduction of AE1-2A.S8 cells by a beta-galactosidase adenoviral vector, its ability to replicate in the presence of DL327Lox was assessed. AE1-2A.S8 cells were transduced with the same CVLs for 72 hours and genomic DNA was subjected to Southern analysis (FIG. 12, middle panel). As was the case above, the use of Cre was associated with a vector band. Most importantly, comparison of the two Southerns demonstrates that the bands were more intense (in comparison to the control lanes) in the second Southern. Therefore, between 4 and 72 hours replication had occurred.

To quantitate the ratio of DL327Lox to beta-galactosidase vector in the CVLs, Southern blot analysis was performed on transduced AE1-2A.S8 cells with a probe that detects both the DL327Lox and the vector. As was noted in the data above, the use of Cre was necessary to detect a vector band. In each case, the DL327Lox band was more intense than the vector band; however, in lanes 3 and 5, the ratio was no more than 10 to 1. Transfection in the absence of Cre resulted in ratios of DL327Lox to vector that were substantially higher. The 10 to 1 ratio of DL327Lox to vector from a single transfection represents very efficient generation of a vector from a transfection and will enable vector production without the need to screen plaques.

Therefore, the data in this example demonstrate that, when used in the manner described above, Cre recombinase can improve dramatically the process of generating an adenoviral vector. Furthermore, this methodology can be used to generate efficiently a vector which is devoid of all adenoviral coding regions.

Example 8

Two steps were undertaken to improve the efficiency with which the adenoviral vector generated by the procedure described above could be amplified in culture. The first, shown in this example, was to lengthen the vector based on the speculation that a minimum length is necessary for the efficient production of functional transducing vector particles. The second, shown in Example 9, was to redesign the packaging signals such that the vector would be preferentially packaged over the DL327Lox.

In order to obtain a vector having a length of about 25 kb, several constructs were prepared. The length of the vector derived from pVNL5 was approximately 17,800 bp. Three longer constructs were prepared which incorporated an albumin-promoted full length Factor VIII cDNA with a small upstream intron from the ApoAI gene. The first two contained both the lambda stuffer sequence and the Factor VIII expression cassette. The third contained the Factor VIII expression cassette but no lambda sequences. In this third construct, a length of approximately 25 kb was obtained by replacing the 950 bp albumin promoter with a 12 kb albumin promoter/enhancer.

Figure 13:
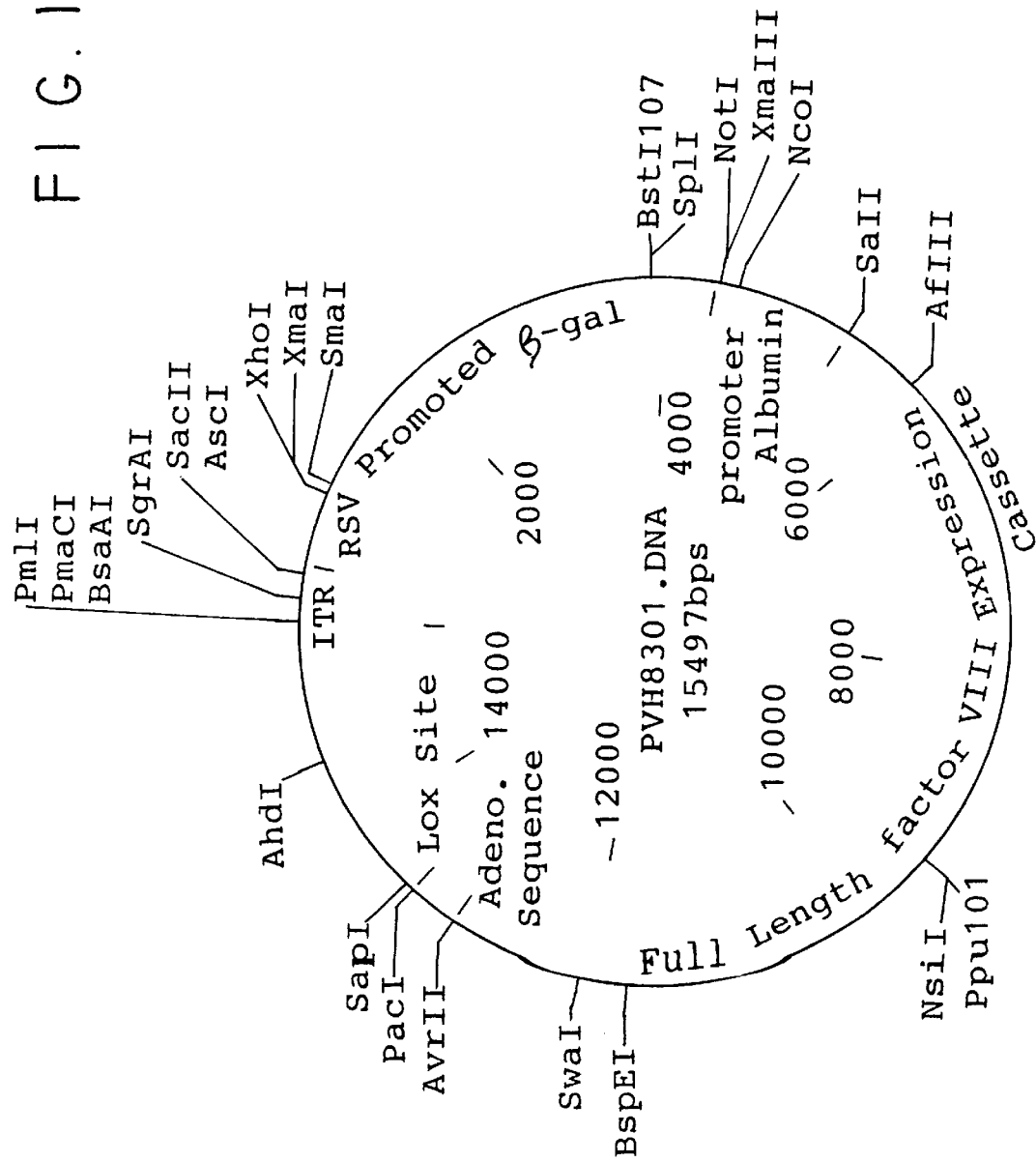
FIG. 13 is a map of plasmid pVH8301.

Several construction steps were involved. First, a full length factor VIII coding region was inserted into the plasmid pAvALAPH81, described in published PCT Application No. WO94/29471, published Dec. 22, 1994, which contains an albumin promoted B domain deleted Factor VIII cDNA and a small upstream intron from the ApoAI gene. The majority of the Factor VIII coding sequence, including the B domain, was removed from the plasmid pSP64-VIII (ATCC No. 39812) as an SpeI to XbaI fragment and swapped with the analogous Factor VIII sequences, without the B domain, in pAvALAPH81. The resultant plasmid, with the full length Factor VIII coding region was termed pAvFVIII. The SV40 polyadenylation signal then was removed from pAvFVIII and replaced with a bovine growth hormone polyadenylation signal from the plasmid pCDNA3.1 (In Vitrogen Corp., San Diego, Calif.). The bovine growth hormone polyadenylation signal was lifted from pCDNA3.1 from bp 1,023 to 1,221 by PCR. A ClaI site was incorporated into the upstream oligonucleotide, and AvrII and XhoI sites were included in the downstream oligonucleotide. This fragment then was inserted into pAvFVIII digested with ClaI and XhoI, thereby replacing the SV40 polyadenylation signal and most of the adenovirus homologous recombination region. The resultant plasmid was termed pAvH83GH. The Factor VIII expression cassette was removed from pAvH83GH as an MluI to AvrII fragment with a NotI linker appended to the MluI site. This fragment was inserted into pVNL6 (FIG. 17, which is identical to pVNL5 except for a small change in the packaging signal; see Example 9 below) as a NotI to AvrII fragment replacing the lambda sequences. The resultant plasmid, pVH8301 (FIG. 13) contained the left adenoviral ITR, packaging signal, RSV-promoted beta-galactosidase gene, SV40 polyadenylation signal, albumin promoter, ApoAI intron, full length Factor VIII coding region, bovine growth hormone polyadenylation signal, a short stretch of right end Adenovirus 5 sequence, and a lox site.

Figure 14:
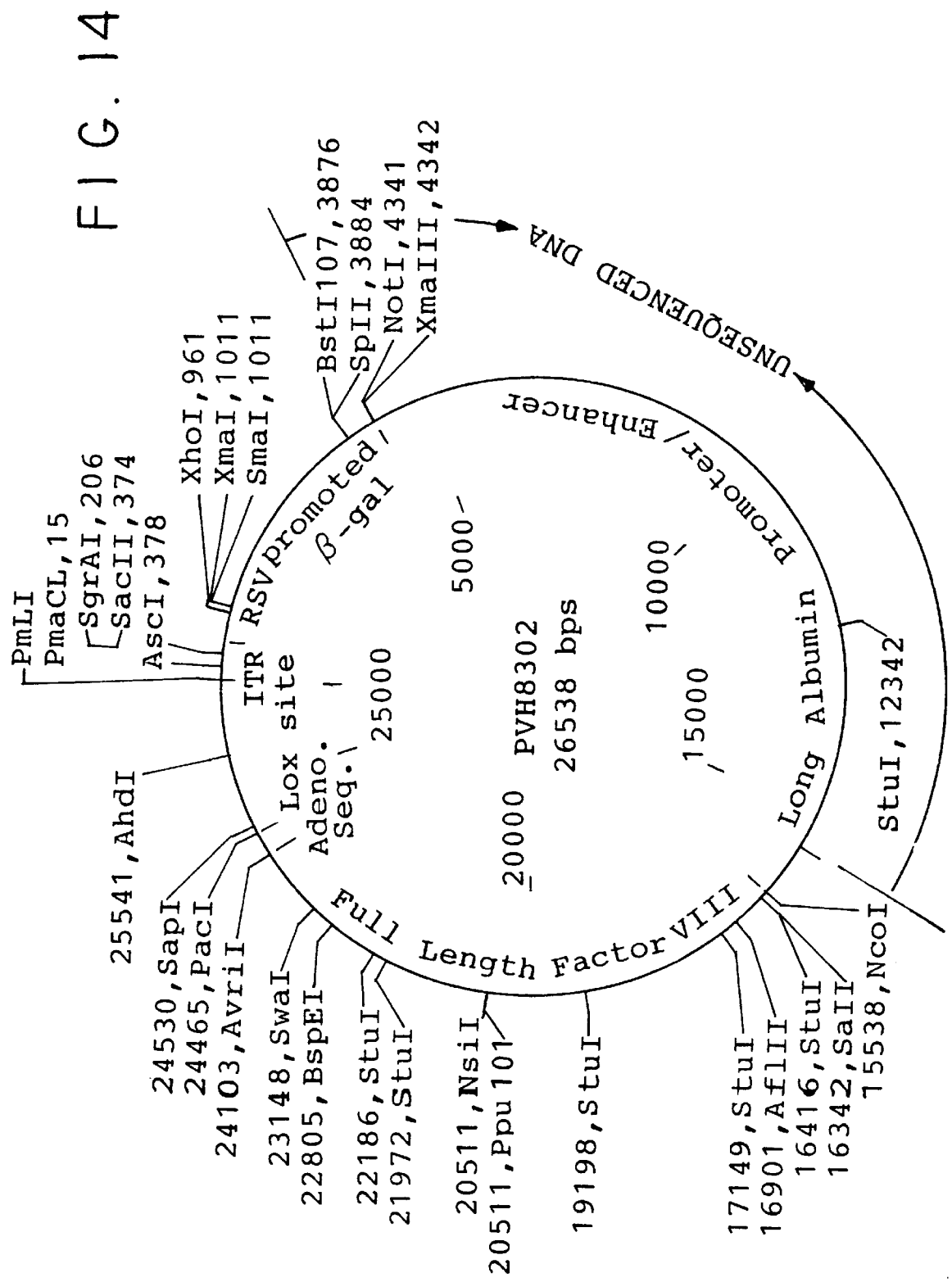
FIG. 14 is a map of plasmid pVH8302.

The length of a vector prepared by this plasmid would have been approximately 13,600 bp. To increase this to 25 kb, several constructs were made. In the first two, termed pV1H8301 and pV2H8301, the 12.9 kb of lambda stuffer DNA was re-inserted into the NotI or AvrII site, respectively, using NotI and AvrII linkers. A third construct was prepared from pVH8301 in which the extra length was not obtained by the insertion of lambda DNA, but by the use, in the Factor VIII expression cassette, of a 12 kb albumin promoter/enhancer sequence described by Pinkert, et al., *Genes and Development*, Vol. 1, pgs. 268–276 (1987). The 12 kb albumin promoter/enhancer was removed from a plasmid which includes the promoter/enhancer as an MluI to BamHI fragment. A NotI linker was appended to the MluI site and a SalI linker was appended to the BamHI site. This 12 kb albumin promoter/enhancer fragment was then inserted into pVH8301 digested with NotI and SalI, thereby replacing the 950 bp albumin promoter. The resultant plasmid was termed pVH8302 (FIG. 14).

The three plasmids, pV1H8301, pV2H8301, and pVH8302, are used with the methodology described in Example 7 to generate adenoviral vectors that are approximately 25 kb long. Each of the resultant vectors is devoid of all adenoviral backbone genes and expresses both beta-galactosidase and human Factor VIII.

Example 9

As noted in Example 8, in addition to lengthening the adenoviral vector, a second step was undertaken to improve the efficiency with which the vectors generated by the procedure described in Example 7 could be amplified in culture. This step involved redesigning the packaging signals such that the vector would be packaged preferentially over the DL327Lox. Several construction steps were involved.

Figure 15:
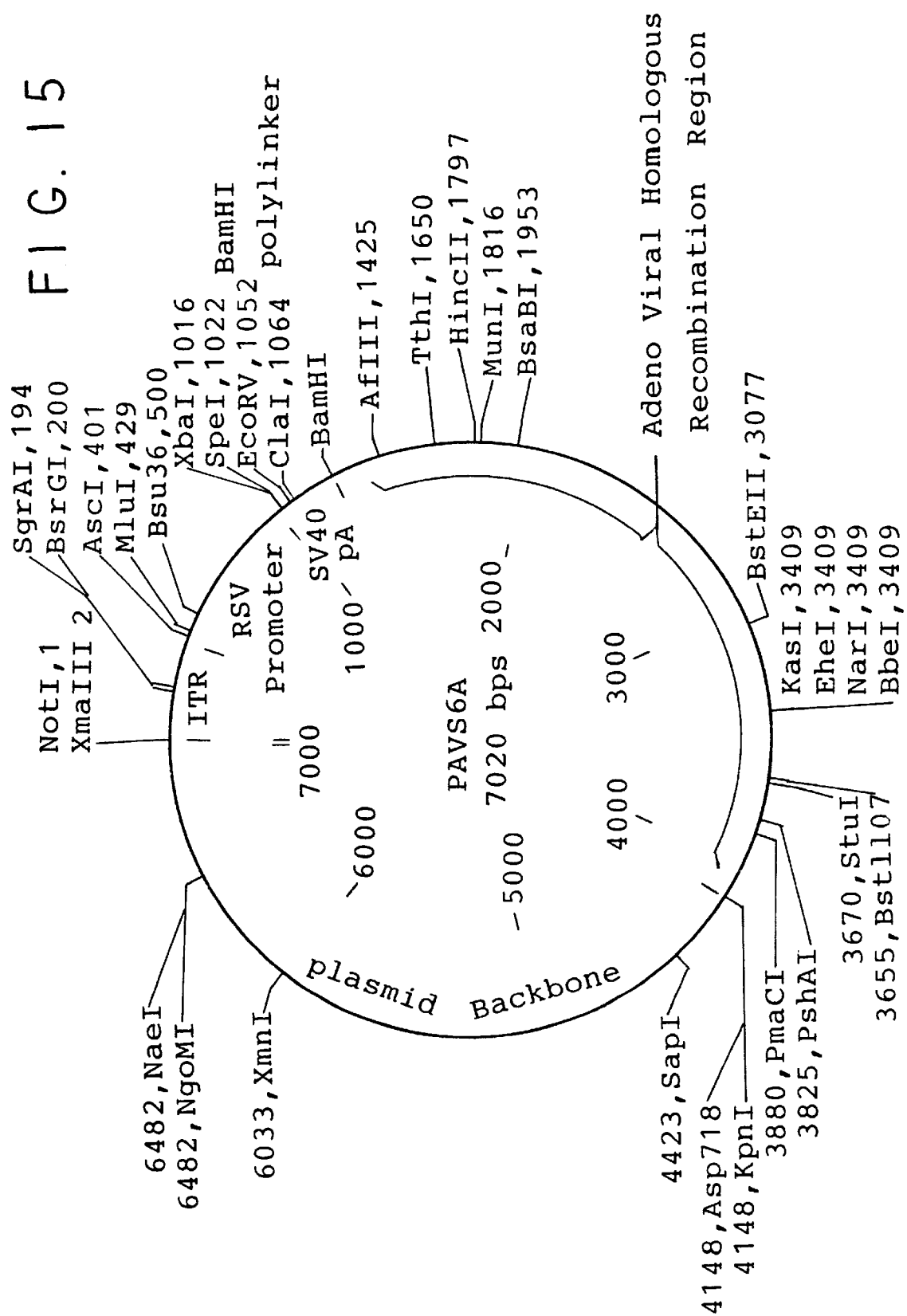
FIG. 15 is a map of plasmid pAvS6A.
Figure 16:
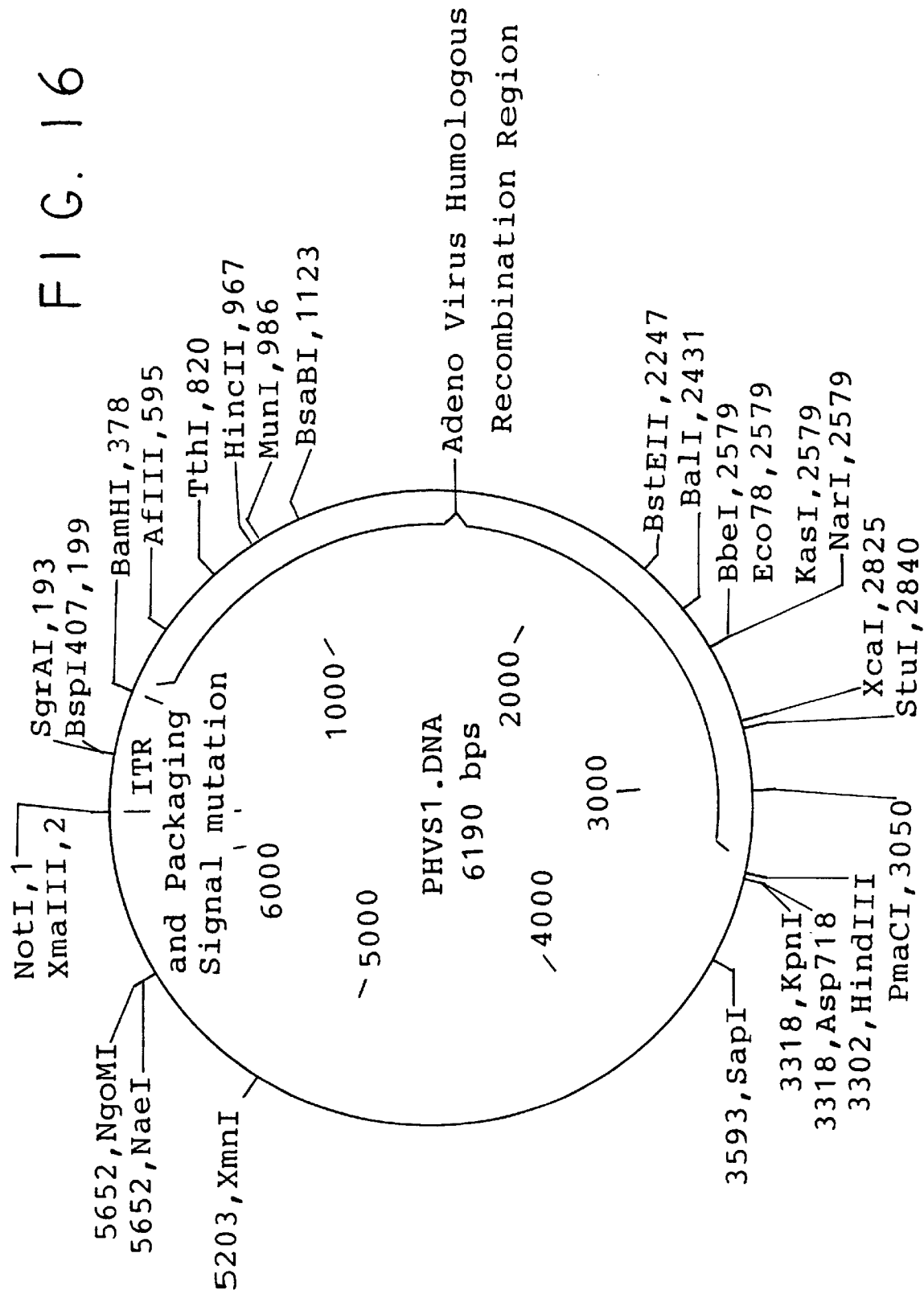
FIG. 16 is a map of plasmid pHVS1.

A new helper virus was generated to replace DL327Lox. This virus, termed LoxHV1 contains the left ITR, packaging signal from bp 102–450 but with a central deletion between bp 267 and 358, the remainder of the Ad5 sequences except for deletions of E1 and E3, and a Lox site in the same position as the Lox site in DL327Lox. Thus, LoxHV1 is an E1, E3 deleted virus with a packaging mutation that diminishes virus packaging by approximately 100 fold. To generate LoxHV1, a fragment containing the packaging signal mutant was lifted by PCR from a plasmid that contained this mutant sequence described by Grable, et al., *Journal of Virology*, Vol. 64, pgs. 2047–2056 (1990). The left oligonucleotide contained a NotI site and the right oligonucleotide contained a BamHI site. The PCR-generated fragment was inserted into pAvS6A (FIG. 15) digested with NotI and BamHI. pAvS6A, described in PCT Application No. WO94/23582, published Oct. 27, 1994, is identical to pAvS6 described in U.S. Pat. No. 5,543,328, except that an ATG at bp 813 was removed by digestion with SfiI, blunting of the 3' overhang, and religation. The resultant plasmid, termed, pHVS1 (FIG. 16), contained the left ITR, the packaging signal to bp 450 but with the central deletion, and the adenovirus homologous recombination region. LoxHV1 virus then was generated by co-transfection of pHVS1 with the large ClaI cut fragment from DL327Lox in AE1-2A.S8 cells. Plaques were picked and expanded. The correct structure was verified by restriction analysis.

The use of AE1-2A.S8 cells for the generation and growth of LoxHV1 was quite important. The E1 expression cassette engineered into these cells starts at Adenovirus 5 bp 552. Thus there is no way that a recombination event with sequences in the cell line could re-insert the wild type packaging signal into LoxHV1. In contrast, if LoxHV1 had been grown on 293 cells, which contain the adenoviral left end, it would be highly likely that recombination would have re-inserted the wild type packaging signal as well as E1 back into LoxHV1. This revertant with its packaging advantage would have overgrown rapidly the LoxHV1.

Figure 17:
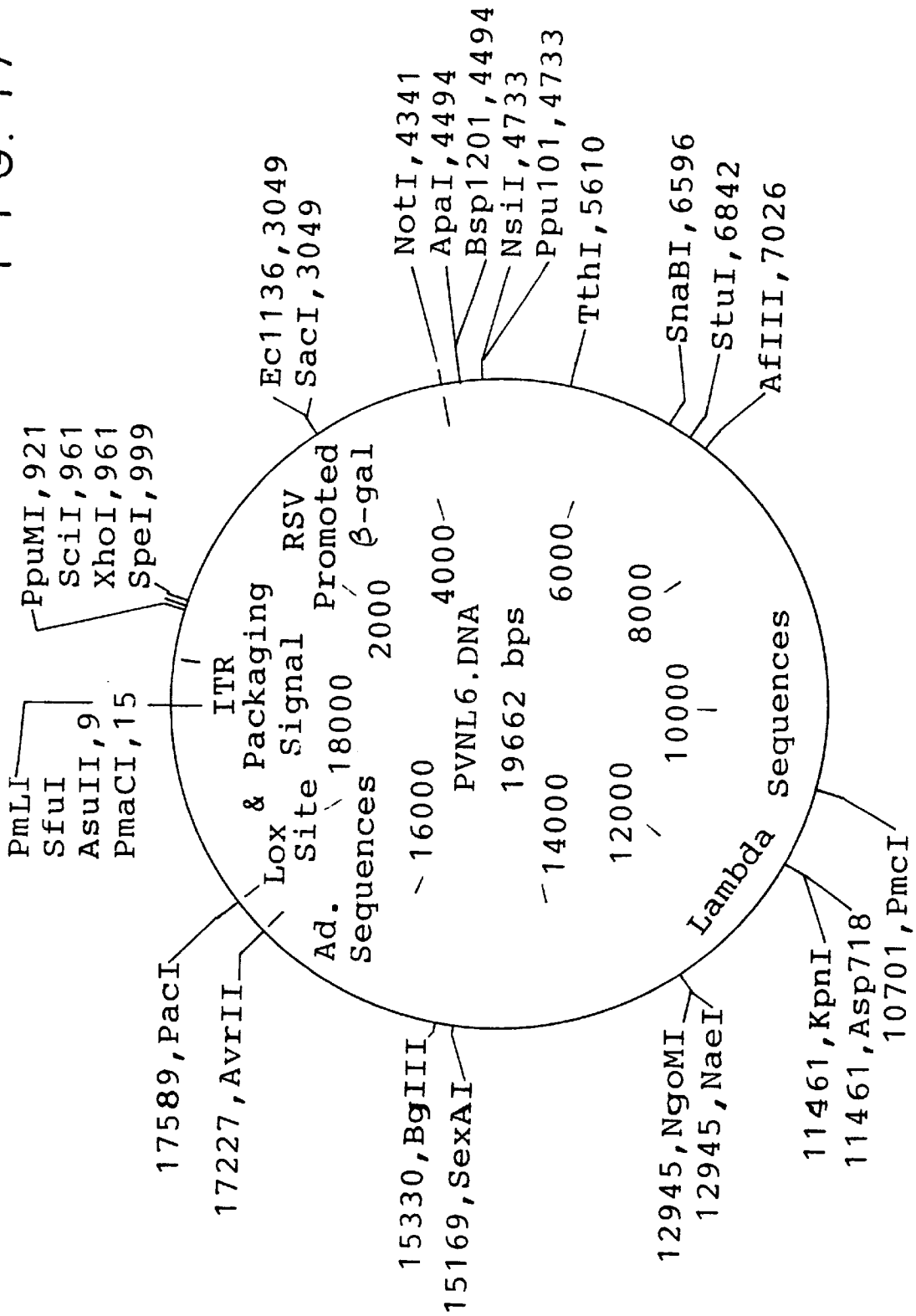
FIG. 17 is a map of plasmid pVNL6.

For the same reason, it was important to modify the packaging signal in pVNL5 to yield pVNL6. The adenoviral packaging signal in pVNL5 extends to Adenovirus 5 bp 393. Thus, there are 35 bp of homology between the packaging signals in pVNL5 and LoxHV1. The growth of a vector derived from pVNL5 in the same cells with LoxHV1 would result in homologous recombination between the vector and LoxHV1 that would re-insert a wild type packaging signal into LoxHV1. To prevent this, the region of homology, bp 358 to 393, was removed from pVNL5 as follows. The first step involved removing the 35 bp from pAvS6A. A fragment which contained Adenovirus 5 bp 1–358 was PCR amplified from pAvS6A. The left oligonucleotide contained NotI, SfuI, and PmlI sites, and the right nucleotide contained an AscI site. This fragment was then swapped with the analogous region of pAvS6A digested with NotI and AscI to yield pAvS6B. This plasmid then was digested with SfuI and SpeI to obtain a fragment containing the ITR, packaging signal, and RSV promoter. This fragment was then swapped with the analogous region of pVNL5 digested with SfuI and SpeI to yield the plasmid pVNL6 (FIG. 17). Thus, pVNL6 is identical to pVNL5 with two exceptions. First, it does not contain the Adenovirus 5 sequence from bp 358–393. Second, it has an additional unique restriction site, PmlI, immediately upstream from the ITR to be used to linearize the plasmid. As noted in Example 8, pVH8301 was constructed with pVNL6. Therefore, its derivatives, pV1H8301, pV2H8301, and pVH8302, all contain the PmlI site and do not contain Adenovirus 5 bp 358–393.

FIG. 18 is a schematic of the packaging signals in pVNL6 and LoxHV1 as well as the E1 expression cassette in the AE1-2A.S8 cells. When pVNL6-derived vectors and LoxHV1 are grown together in these cells, re-insertion of a wild type packaging signal into LoxHV1 by homologous recombination is not possible.

Figure 19:
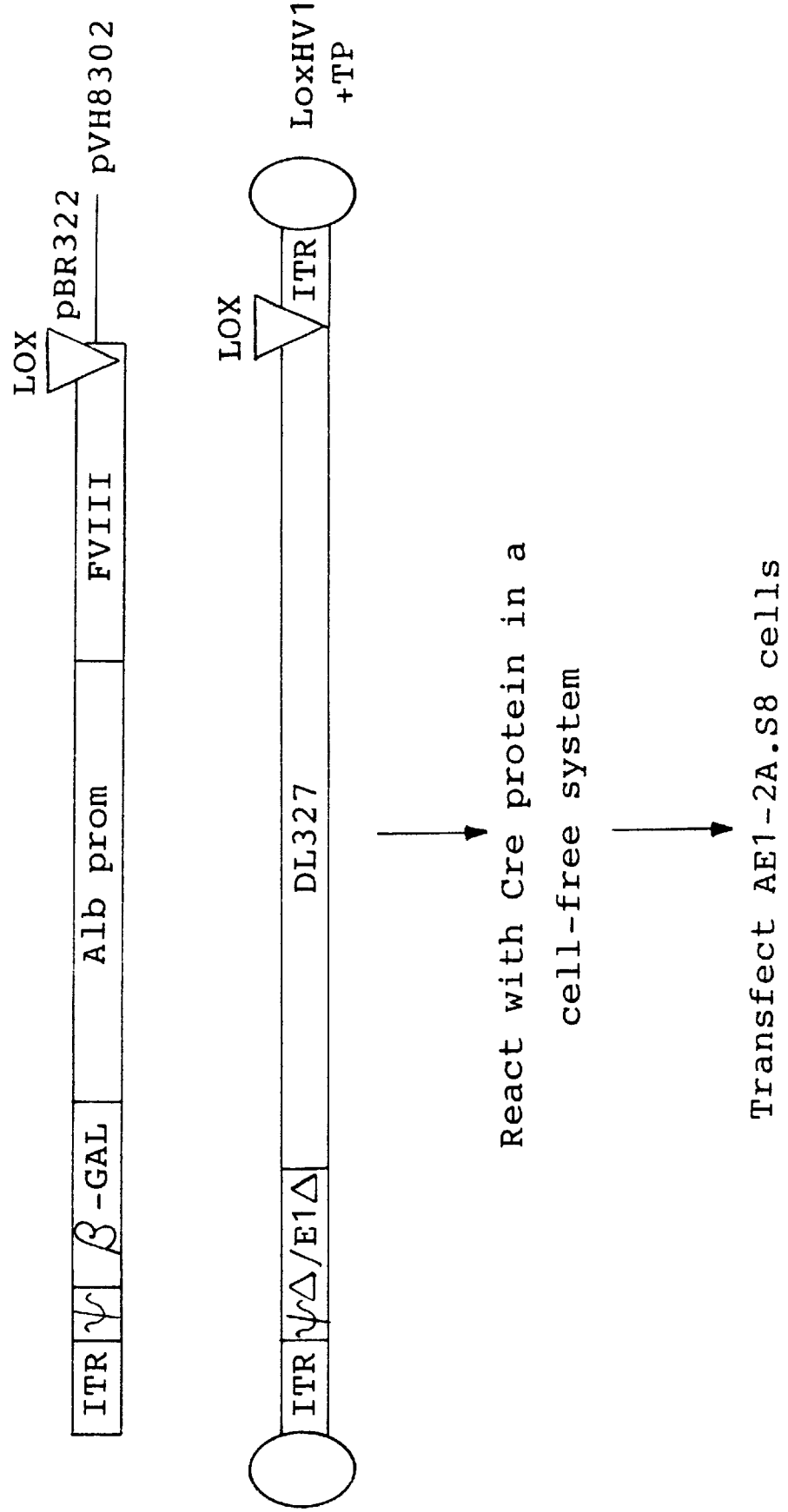
FIG. 19 is a schematic of the reaction of pVH8302 and LoxHV1 with terminal proteins with cre recombinase in a cell-free system, followed by transfection of AE1-2A.S8 cells.

Each of the three plasmids, pV1H8301, pV2H8301, and pVH8302, are used in combination with LoxHV1 and Cre recombinase, to generate an adenoviral vector that contains no adenoviral backbone genes and expresses both beta-galactosidase and human Factor VIII. Vector generation is rapid and requires no plaque screening. The procedure is as follows and is shown schematically for pVH8302 (FIG. 19).

DNA with terminal proteins intact is obtained from a viral preparation of LoxHV1 by the procedure outlined in Example 3. The plasmid pVH8302 (or pV1H8301 or pV2H8301) is linearized with PmlI because SfuI which had been used for linearization in the previous examples is not unique in plasmids that contain the Factor VIII cDNA. The linearized DNA then is purified by phenol/chloroform and chloroform extractions, ethanol precipitation, and resuspension in TE (10 mM Tris, pH 8 and 1 mM EDTA). 2 µg of LoxHV1 DNA with terminal proteins intact and 2 µg of linearized plasmid then are reacted with a 25 fold molar excess of Cre as described in Example 7 above. Using the Promega (Madison, Wis.) calcium phosphate transfection kit, the reaction mixture then is transfected into AE1-2A.S8 cells. The cells had been plated in a 6 cm tissue culture dish two days prior to transfection and dexamethasone had been added to their media to a concentration of 300 µg/ml one day prior to transfection. Dexamethasone serves to induce the expression of E1 and E2a in these cells. At the time of transfection, the cells are 30–506% confluent.

Approximately 16 hours after transfection, the calcium phosphate precipitate is washed from the tissue culture dish, and three days after transfection the cells are harvested. A CVL is prepared by 5 freeze thaw cycles and is placed on dexamethasone induced AE1-2A.S8 cells in a 10 cm dish. When the cells demonstrate cytopathic effects (CPE), a CVL is prepared and used to infect dexamethasone induced AE1-2A.S8 cells on four 15 cm dishes. The CVL from these dishes then is used to infect forty 15 cm dishes. The cell pellet from these dishes is used to make an adenoviral preparation by standard methodology that involves a CsCl step gradient followed by a CsCl equilibrium density gradient. With this procedure the vector is separated readily from the LoxHV1. Since the vector is shorter than LoxHV1, it bands higher in the gradient. Additionally, the vector band is larger than the LoxHV1 band because the LoxHV1 virus is packaged poorly.

The integrity of the adenoviral vector prepared by this procedure is verified by restriction analysis of the DNA obtained from the vector. Its titer is determined from a spectrophotometric measurement of its DNA content and by beta-galactosidase expression in vector-transduced cells. Additionally, Factor VIII expression in transduced cells provides a measure of the vector's potency. The extent to which the vector preparation is contaminated by LoxHV1 is determined by restriction and PCR analyses of the DNA obtained from the vector preparation and by staining vector transduced AE1-2A.S8 (or 293) cells for hexon expression.

Example 10

This is an example which uses the large transgene encoding capacity of the vectors described herein to enable the preparation of a hybrid adenoviral-retroviral (HARV) vector. Such a vector combines the high transduction efficiency of adenoviral vectors with the capacity of retroviral vectors to modify a target cell genome permanently. Specifically, each cell transduced with the HARV vector would generate a retroviral vector encoding a marker or therapeutic transgene. The retroviral vector would then spread the transgene to the neighboring cells and integrate it permanently into their genomic DNA. The transgene used in this example is B domain deleted Factor VIII.

Figure 20:
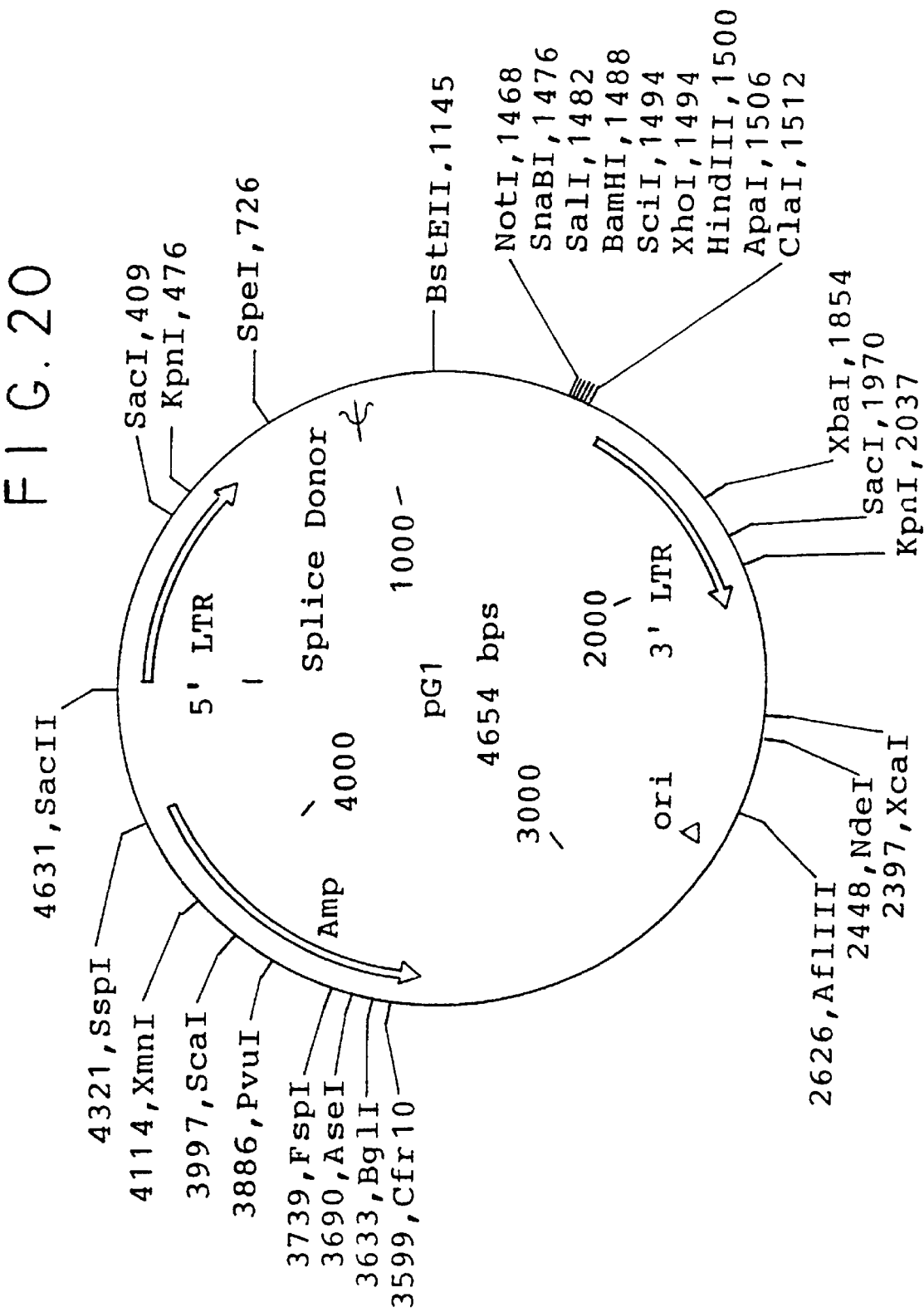
FIG. 20 is a map of plasmid pG1.

The retroviral construct in this example is a derivative of the Moloney Murine Leukemia Virus (MMLV) retroviral backbone plasmid pG1 (FIG. 20, and described in PCT Application No. WO91/10728, published Jul. 25, 1991) that utilizes the natural envelope splice site. This construct is termed pG1S.

Figure 21:
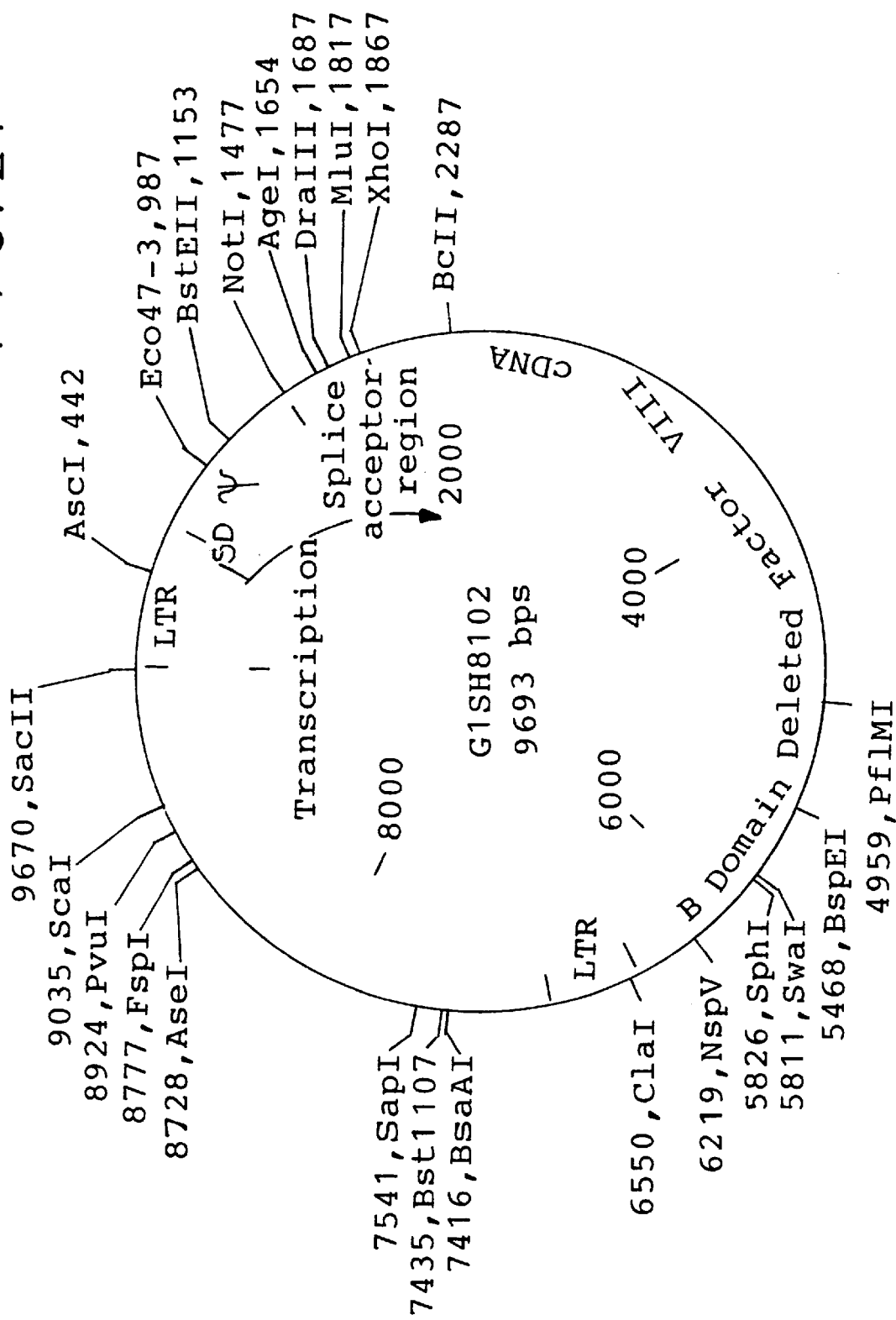
FIG. 21 is a map of plasmid pG1SH8102.
Figure 22:
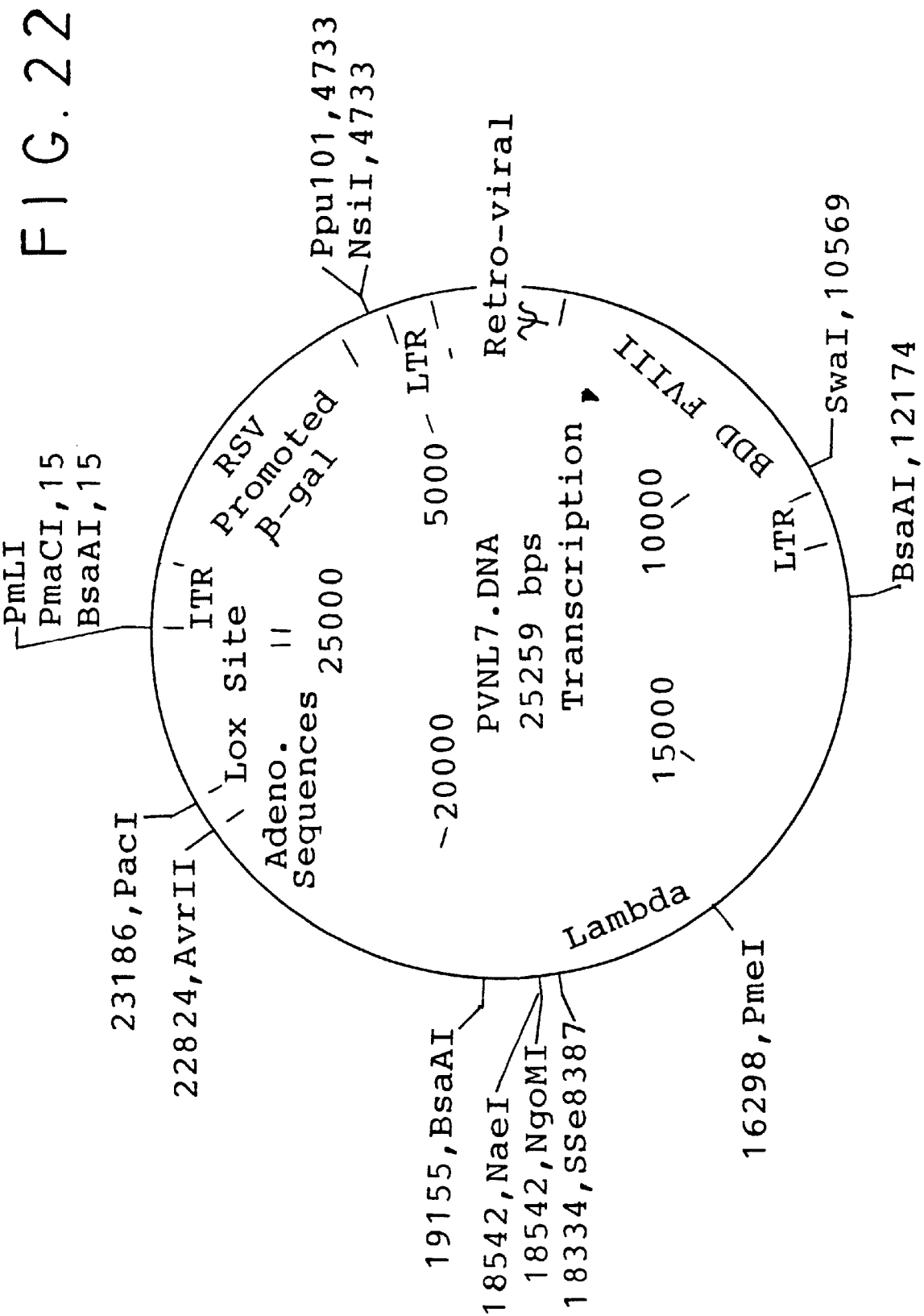
FIG. 22 is a map of plasmid pVNL7.
Figure 23:
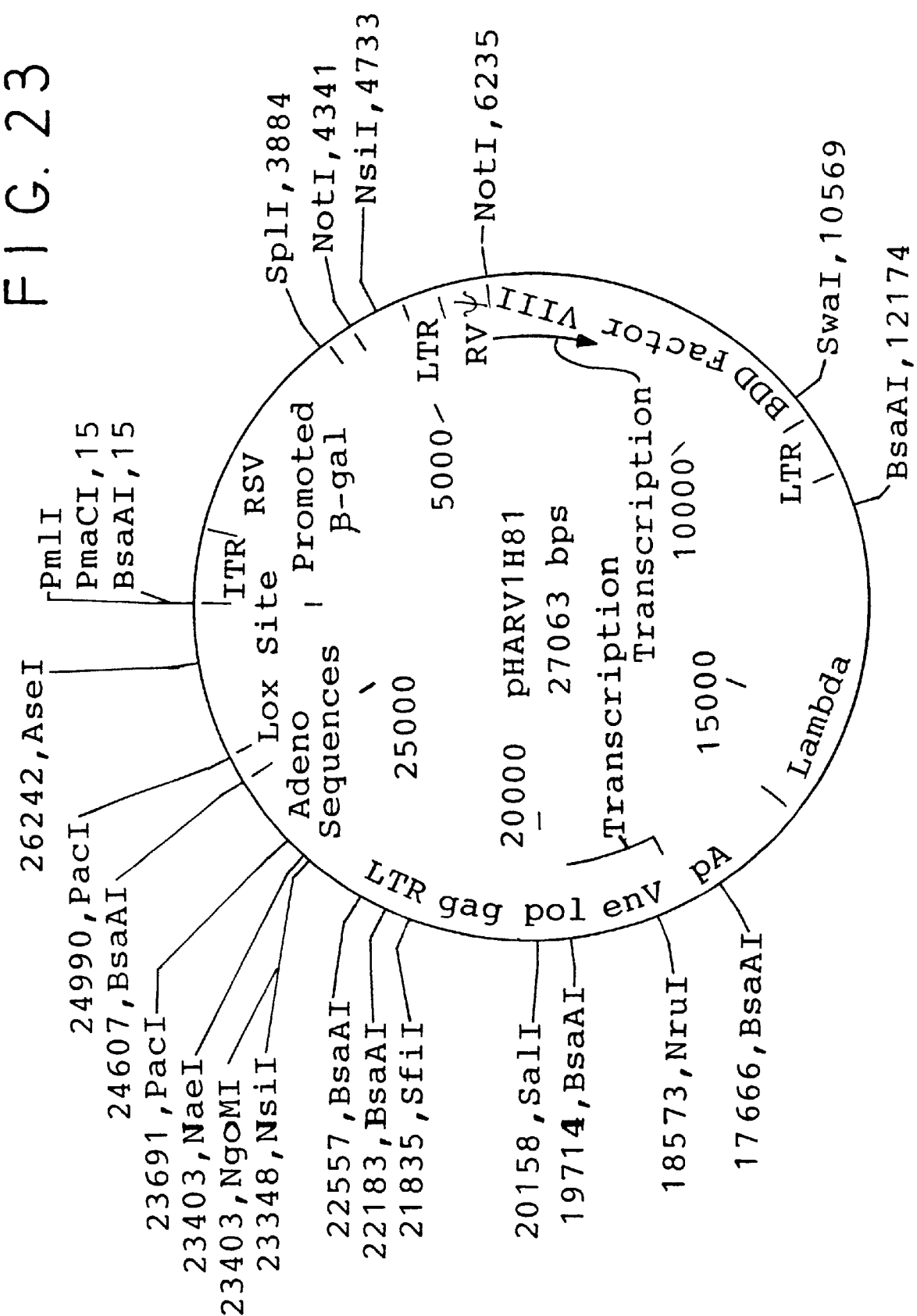
FIG. 23 is a map of plasmid pHARV1H81.

To prepare pG1S, a fragment containing the natural MMLV splice acceptor is lifted from MMLV by PCR. The amplified region extends from MMLV bp 5401–5776. The upstream oligonucleotide contains a NotI site and the downstream oligonucleotide contains an XhoI site. This fragment is then inserted into pG1 (FIG. 20) digested with NotI and XhoI, yielding pG1S. B domain deleted factor VIII is then inserted into the retroviral construct by removing the factor VIII coding region from pMT2LA (obtained from Genetics Institute, Cambridge, Mass., and described in PCT Application No. WO94/29471) as an XhoI to SalI fragment and ligating it into G1S cut with XhoI. The resultant plasmid is termed pG1SH8101. The PmlI site in the MMLV splice acceptor region is removed by digestion with PmlI and religation across an MluI linker to yield pG1SH8102 (FIG. 21). The Factor VIII-containing retroviral construct then is removed from pG1SH8102 by digestion with SacII and Bst1107, and an NsiI linker is appended to the SacII site. This fragment is then ligated into pVNL6 cut with NsiI and SnaBI to yield pVNL7 (FIG. 22). The expression cassette for the retroviral packaging genes gag, pol, and env is removed from pPAM3 (Miller et al., *Biotechniques*, Vol. 7, pgs. 980–990 (1989)) as an NheI to Bst1107 fragment, and the NheI site is blunted. This fragment is ligated into pVNL7 cut with PmeI and AvrII, with the AvrII site blunted. The resultant plasmid, termed pHARV1H81 is shown in FIG. 23.

Figure 24:
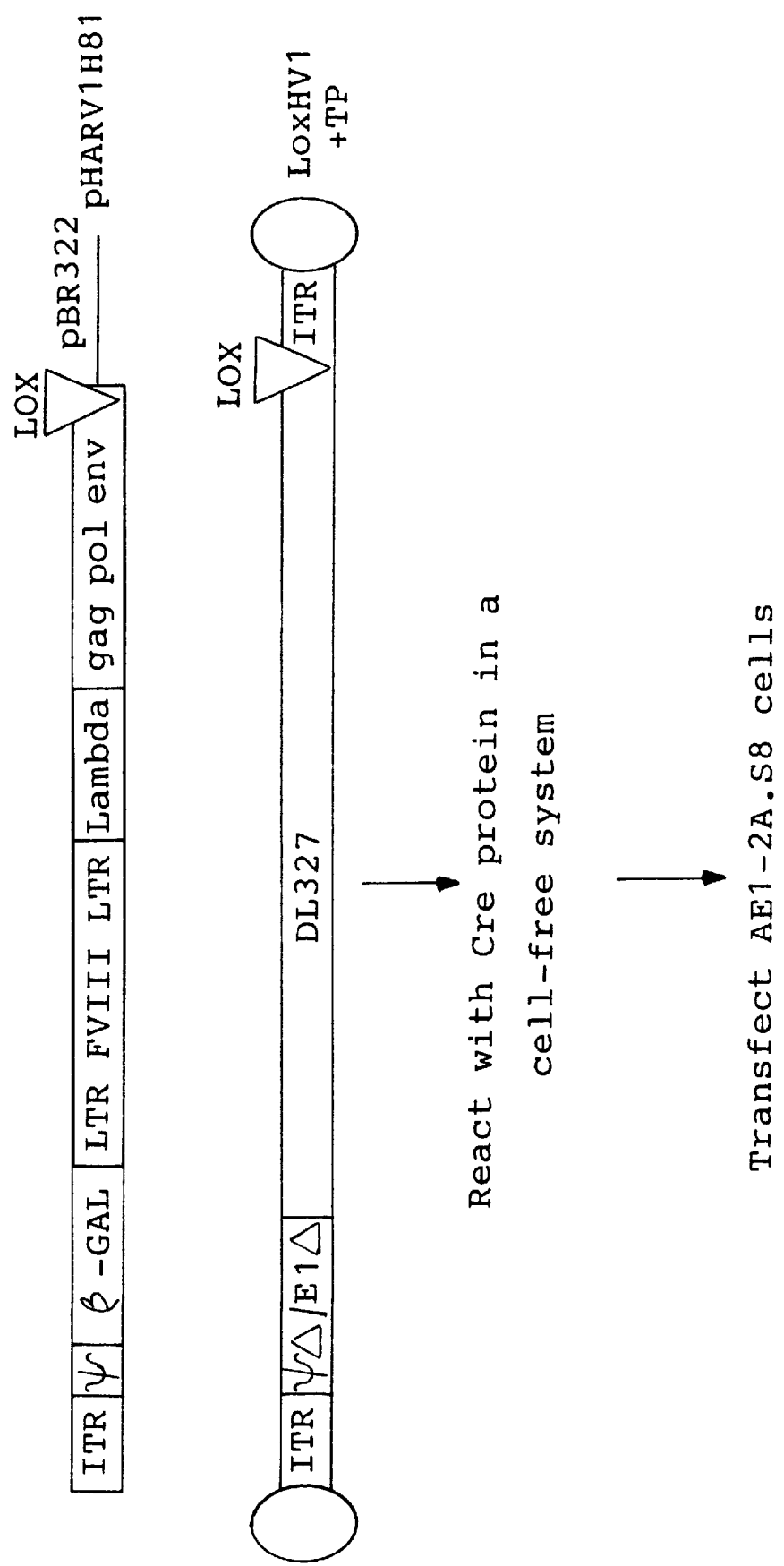
FIG. 24 is a schematic of the reaction of pHARV1H81 and LoxHV1 with terminal proteins with cre recombinase in a cell-free system, followed by transfection of AE1-2A.S8 cells.

The preparation of the HARV vector is exactly analogous to the preparation of vectors in Example 9. Briefly, PmlI linearized pHARV1H81 and LoxHV1 DNA with terminal proteins intact are reacted with an excess of Cre protein and then transfected into AE1-2A.S8 cells (FIG. 24). Three days later a CVL is prepared and the preparation is taken through several rounds of amplification on a 10 cm dish, four 15 cm dishes, and forty 15 cm dishes. The vector then is purified by ultracentrifugation and its integrity is verified by the quality control assays outlined in Example 9.

When injected into the tail vein of a mouse, the HARV1H81 vector accumulates in hepatocytes. The injected dose of approximately $10^8$ particles is chosen to transduce approximately 1% of hepatocytes. The HARV1H81 transduced cells secrete a retroviral vector that encodes B domain deleted human Factor VIII. This retroviral vector then transduces and modifies the surrounding hepatocytes permanently. In juvenile mice, normal liver growth results in sufficient hepatocyte cell division to enable efficient hepatocyte transduction with the retroviral vector. In adult animals, hepatocyte proliferation can be achieved by intravenous administration of growth factors such as keratinocyte growth factor.

The disclosure of all patents, publications, (including published patent applications), and database accession numbers and depository accession numbers referenced in this specification are specifically incorporated herein by reference in their entirety to the same extent as if each such individual patent, publication, and database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A hybrid adenoviral-retroviral vector including:
an adenoviral 5' ITR;
an adenoviral packaging signal;
a retroviral 5' LTR;
a retroviral packaging signal;
a DNA sequence encoding a protein heterologous to adenovirus and retrovirus;
a retroviral 3' LTR;
a DNA sequence encoding a retroviral gag protein and a retroviral pol protein;
a DNA sequence encoding a retroviral env protein; and an adenoviral 3' ITR, wherein (i) said adenoviral 5' ITR and said adenoviral 3' ITR flank said adenoviral packaging signal, said retroviral 5' LTR, said retroviral packaging signal, said DNA sequence encoding said protein heterologous to adenovirus and retrovirus, said retroviral 3' LTR, said DNA sequence encoding a retroviral gag protein and a retroviral pol protein, and said DNA sequence encoding a retroviral env protein; (ii) said retroviral 5' LTR and said retroviral 3' LTR flank said retroviral packaging signal and said DNA encoding a protein heterologous to adenovirus and retrovirus; (iii) said DNA sequence encoding a retroviral gag protein and a retroviral pol protein and said DNA sequence encoding the retroviral env protein are not flanked by said retroviral 5' LTR and said retroviral 3' LTR; and (iv) said adenoviral packaging signal is not flanked by said retroviral 5' LTR and said retroviral 3' LTR and is located sufficiently proximal to one of said adenoviral 5' ITR or said adenoviral 3' ITR to enable said hybrid adenoviral-retroviral vector to be packaged.

2. A method of generating a hybrid adenoviral-retroviral vector, comprising:
transfecting into a cell:
(a) a first polynucleotide including a retroviral 5' LTR, a retroviral packaging signal, a DNA sequence encoding at least one protein or polypeptide heterologous to adenovirus and retrovirus, a retroviral 3' LTR; a DNA sequence encoding a retroviral gag protein and a retroviral pol protein, a DNA sequence encoding a retroviral env protein, an adenoviral ITR, an adenoviral packaging signal, and a recombinase target site;
(b) a second polynucleotide including at least one adenoviral ITR, which includes a terminal protein bound to said ITR, and a recombinase target site, wherein said ITR is a 5' ITR when said first polynucleotide includes an adenoviral 3' ITR, and said ITR is a 3' ITR when said first polynucleotide includes an adenoviral 5' ITR; and
(c) a third polynucleotide including DNA encoding a site-specific recombinase, wherein said cell contains DNA encoding adenoviral proteins for replication and packaging of said first polynucleotide as an adenoviral vector to the extent such DNA is not present in said first, second, and third polynucleotides, whereby upon transfection of said cell with said first, second, and third polynucleotides, an adenoviral ITR which includes a terminal protein bound to said ITR is transferred from said second polynucleotide to said first polynucleotide, thereby generating a hybrid adenoviral-retroviral vector from said first polynucleotide.

3. The method of claim 2 wherein said DNA encoding adenoviral proteins for replication and packaging of said first polynucleotide as a hybrid adenoviral-retroviral vector is included in said second polynucleotide.

4. The method of claim 2 wherein said DNA encoding adenoviral proteins for replication and packaging of said first polynucleotide as a hybrid adenoviral-retroviral vector is included in said first polynucleotide.

5. The method of claim 2 wherein a portion of said DNA encoding adenoviral proteins for replication and packaging of said first polynucleotide as a hybrid adenoviral-retroviral vector is included in said first polynucleotide, and a portion of said DNA encoding adenoviral proteins for replication and packaging of said first polynucleotide as a hybrid adenoviral-retroviral vector is included in said second polynucleotide.

6. The method of claim 2 wherein a portion of said DNA encoding adenoviral proteins for replication and packaging of said first polynucleotide as a hybrid adenoviral-retroviral vector is provided by said cell.

7. The method of claim 2 wherein said site-specific recombinase is Cre recombinase and the recombinase target site is a Lox site.

8. A hybrid adenoviral-retroviral vector generated according to the method of claim 2.

9. The method of claim 2 wherein said first polynucleotide is a plasmid.

10. The method of claim 9 wherein said plasmid is free of DNA encoding adenoviral proteins and free of DNA encoding selectable markers, and said second polynucleotide is a helper virus including an adenoviral 5' ITR, an adenoviral packaging signal, DNA encoding adenoviral proteins for replication and packaging of said plasmid as a hybrid adenoviral-retroviral vector, a recombinase target site, and an adenoviral 3' ITR, wherein an adenoviral terminal protein is bound to at least one of the adenoviral 5' ITR and 3' ITR.

11. A method of generating a hybrid adenoviral-retroviral vector, comprising:
(a) reacting with a site-specific recombinase:
(i) a first polynucleotide including a retroviral 5' LTR, a retroviral packaging signal, a DNA sequence encoding a protein or polypeptide heterologous to adenovirus and retrovirus, a retroviral 3' LTR, a DNA sequence encoding a retroviral gag protein and a retroviral pol protein, a DNA sequence encoding a retroviral env protein, an adenoviral ITR, an adenoviral packaging signal, and a recombinase target site; and
(ii) a second polynucleotide including at least one adenoviral ITR, which includes a terminal protein bound to said ITR, and a recombinase target site, wherein said ITR is a 5' ITR when said first polynucleotide includes an adenoviral 3' ITR, and said ITR is a 3' ITR when said first polynucleotide includes an adenoviral 5' ITR, whereby upon reaction of said first polynucleotide and said second polynucleotide with said site specific recombinase, an adenoviral ITR which includes a terminal protein bound to said ITR is transferred from said second polynucleotide to said first polynucleotide; and
(b) transfecting into a cell, after reacting said first polynucleotide and said second polynucleotide, said first polynucleotide and said second polynucleotide, said cell containing DNA encoding adenoviral proteins for replication and packaging of said first polynucleotide as a hybrid adenoviral-retroviral vector to the extent such DNA is not present in said first and second polynucleotides, and whereby upon transfection of said cell with said first and second polynucleotides, a hybrid adenoviral-retroviral vector is generated from said first polynucleotide.

12. The method of claim 11 wherein said DNA encoding adenoviral proteins for replication and packaging of said first polynucleotide as a hybrid adenoviral-retroviral vector is included in said second polynucleotide.

13. A hybrid adenoviral-retroviral vector generated according to the method of claim 11.

14. An adenoviral vector for expressing heterologous DNA, said adenoviral vector having been generated by the method comprising:
(a) reacting with a site-specific recombinase:
(i) a first polynucleotide including heterologous DNA, said heterologous DNA including a retroviral 5' LTR, a retroviral packaging signal, a DNA sequence encoding a protein heterologous to adenovirus and retrovirus, a retroviral 3' LTR, a DNA sequence encoding a retroviral gag protein and a retroviral pol protein, and a DNA sequence encoding a retroviral env protein, wherein said retroviral 5' LTR and said retroviral 3' LTR flank said retroviral packaging signal and said DNA sequence encoding a protein heterologous to retrovirus and adenovirus, and wherein said DNA sequence encoding a retroviral gag protein and a retroviral pol protein and said DNA sequence encoding a retroviral env protein are not flanked by said retroviral 5' LTR and said retroviral 3' LTR; an adenoviral ITR, an adenoviral packaging signal, and a recombinase target site; and (ii) a second polynucleotide including at least one adenoviral ITR, which includes a terminal protein bound to said ITR, and a recombinase target site, wherein said ITR is a 5' ITR when said first polynucleotide includes an adenoviral 3' ITR, and said ITR is a 3' ITR when said first polynucleotide includes an adenoviral 5' ITR, whereby upon reaction of said first polynucleotide and said second polynucleotide with said site specific recombinase, an adenoviral ITR which includes a terminal protein bound to said ITR is transferred from said second polynucleotide to said first polynucleotide; and (b) transfecting into a cell, after reacting said first polynucleotide and said second polynucleotide, said first polynucleotide and said second polynucleotide, said cell containing DNA encoding adenoviral proteins for replication and packaging of said first polynucleotide as an adenoviral vector to the extent such DNA is not present in said first and second polynucleotides, and whereby upon transfection of said cell with said first and second polynucleotides, an adenoviral vector is generated from said first polynucleotide.

* * * * *

```
                         SEQUENCE LISTING (1) GENERAL INFORMATION:

(iii) NUMBER OF SEQUENCES:  7

(2) INFORMATION FOR SEQ ID NO: 1:

(i) SEQUENCE CHARACTERISTICS:
          (A) LENGTH: 27 bases
          (B) TYPE:  nucleic acid
          (C) STRANDEDNESS:  single
          (D) TOPOLOGY:  linear (ii) MOLECULE TYPE:  oligonucleotide (ix) FEATURE:
          (A) NAME/KEY:  PCR primer (xi) SEQUENCE DESCRIPTION:  SEQ ID NO: 1:

GGTTAATTAA GAAAACTACA ATTCCCA                                         27

(2) INFORMATION FOR SEQ ID NO: 2:

(i) SEQUENCE CHARACTERISTICS:
          (A) LENGTH: 36 bases
          (B) TYPE:  nucleic acid
          (C) STRANDEDNESS:  single
          (D) TOPOLOGY:  linear (ii) MOLECULE TYPE:  oligonucleotide (ix) FEATURE:
          (A) NAME/KEY:  PCR primer (xi) SEQUENCE DESCRIPTION:  SEQ ID NO: 2:

GTGGGATCCA TCATCAATAA TATACCTTAT TTTGGA                               36

(2) INFORMATION FOR SEQ ID NO: 3:

(i) SEQUENCE CHARACTERISTICS:
          (A) LENGTH: 21 bases
          (B) TYPE:  nucleic acid
          (C) STRANDEDNESS:  single
          (D) TOPOLOGY:  linear (ii) MOLECULE TYPE:  oligonucleotide (ix) FEATURE:
          (A) NAME/KEY:  PCR primer (xi) SEQUENCE DESCRIPTION:  SEQ ID NO: 3:

TAAGCTCCGG AACCACCACA G                                               21

(2) INFORMATION FOR SEQ ID NO: 4:
```

-continued

```
    (i) SEQUENCE CHARACTERISTICS:
        (A) LENGTH: 31 bases
        (B) TYPE:  nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 4:

GGTTAATTAA AATGGGAAGT GACGTAACGT G                                   31

(2) INFORMATION FOR SEQ ID NO: 5:

(i) SEQUENCE CHARACTERISTICS:
        (A) LENGTH: 39 bases
        (B) TYPE:  nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

ATAACTTCGT ATAATGTATG CTATACGAAG TTATTTAAT                            39

(2) INFORMATION FOR SEQ ID NO: 6:

(i) SEQUENCE CHARACTERISTICS:
        (A) LENGTH: 39 bases
        (B) TYPE:  nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 6:

TAAATAACTT CGTATAGCAT ACATTATACG AAGTTATAT                            39

(2) INFORMATION FOR SEQ ID NO: 7:

(i) SEQUENCE CHARACTERISTICS:
        (A) LENGTH: 300 bases
        (B) TYPE:  nucleic acid
        (C) STRANDEDNESS: single
        (D) TOPOLOGY: linear (ii) MOLECULE TYPE: oligonucleotide (ix) FEATURE:
        (A) NAME/KEY: Adenoviral E4 promoter (xi) SEQUENCE DESCRIPTION: SEQ ID NO: 7:

CATCATCAAT AATATACCTT ATTTTGGATT GAAGCCAATA TGATAATGAG GGGGTGGAGT     60

TTGTGACGTG GCGCGGGGCG TGGGAACGGG GCGGGTGACG TAGGTTTTAG GGCGGAGTAA    120

CTTGTATGTG TTGGGAATTG TAGTTTTCTT AAAATGGGAA GTGACGTAAC GTGGGAAAAC    180

GGAAGTGACG ATTTGAGGAA GTTGTGGGTT TTTTGGCTTT CGTTTCTGGG CGTAGGTTCG    240

CGTGCGGTTT TCTGGGTGTT TTTTGTGGAC TTTAACCGTT ACGTCATTTT TTAGTCCTAT    300
```